US007678960B2

(12) United States Patent
Davies et al.

(10) Patent No.: US 7,678,960 B2
(45) Date of Patent: Mar. 16, 2010

(54) GENERATION OF PLANTS WITH ALTERED OIL, PROTEIN, OR FIBER CONTENT

(75) Inventors: John P. Davies, Portland, OR (US); Hein Tsoeng (Medard) Ng, Charlottesville, VA (US)

(73) Assignee: Agrinomics LLC, Portland, OR (US)

( * ) Notice: Subject to any disclaimer, the term of this patent is extended or adjusted under 35 U.S.C. 154(b) by 0 days.

(21) Appl. No.: 12/483,524

(22) Filed: Jun. 12, 2009

(65) Prior Publication Data

US 2009/0287008 A1 Nov. 19, 2009

Related U.S. Application Data

(62) Division of application No. 11/956,228, filed on Dec. 13, 2007, now Pat. No. 7,563,943.

(60) Provisional application No. 60/870,355, filed on Dec. 15, 2006.

(51) Int. Cl.
*C12N 15/82* (2006.01)
*C12N 15/87* (2006.01)

(52) U.S. Cl. ................. 800/281; 800/278; 435/468

(58) Field of Classification Search ................. None
See application file for complete search history.

(56) References Cited

U.S. PATENT DOCUMENTS

| | | | |
|---|---|---|---|
| 5,322,783 | A | 6/1994 | Tomes et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,610,042 | A | 3/1997 | Chang et al. |
| 5,639,790 | A | 6/1997 | Voelker et al. |
| 5,704,160 | A | 1/1998 | Bergquist et al. |
| 5,952,544 | A | 9/1999 | Browse et al. |
| 6,229,033 | B1 | 5/2001 | Knowlton |
| 6,248,939 | B1 | 6/2001 | Leto et al. |
| 2004/0025202 | A1 | 2/2004 | Laurie et al. |
| 2006/0150283 | A1* | 7/2006 | Alexandrov et al. ........ 800/288 |
| 2006/0277630 | A1 | 12/2006 | Lightner et al. |

FOREIGN PATENT DOCUMENTS

| | | |
|---|---|---|
| EP | 1033405 | 9/2000 |
| WO | 94/11516 | 5/1994 |
| WO | 95/06128 | 3/1995 |
| WO | 2004/093528 | 11/2004 |
| WO | 2004/093532 | 11/2004 |
| WO | 2005/107437 | 11/2005 |
| WO | 2007/053482 | 5/2007 |

OTHER PUBLICATIONS

Anoop et al., "Modulation of citrate metabolism alters aluminum tolerance in yeast and transgenic canola overexpressing a mitochondrial citrate synthase," *Plant Physiol.* 132, 2205-2217 (2003).

Bateman et al., "Pfam 3.1: 1313 multiple alignments and profile HMMs match the majority of proteins," *Nucleic Acids Res.*, 27:260-262, 1999.

Beisson, et al., "*Arabidopsis* genes involved in acyl lipid metabolism. A 2003 census of the candidates, a study of the distribution of expressed sequence tags in organs, and a web-based database," *Plant Physiol.*, 132:681-697 (2003).

Bert et al., "Comparative genetic analysis of quantitative traits in sunflower (*Helianthus annuus* L.). 2. Characterisation of QTL involved in developmental and agronomic traits," *Theor. Appl. Genet.*, 107:181-9, (2003).

Browse et al., "Fluxes through the prokaryotic and eukaryotic pathways of lipid synthesis in the '16:3' plant *Arabidopsis thaliana*," *Biochem J.* 235:25-31 (1986).

Chapple and Carpita, "Plant cell walls as targets for biotechnology," *Current Opinion in Plant Biology*, 1:179-185 (1998).

Christensen et al., *9th International Conference on Arabidopsis Research*, Univ. of Wisconsin-Madison, Jun. 24-28, Abstract 165 (1998).

Christou et al., "Inheritance and expression of foreign genes in transgenic soybean plants," *Proc. Natl. Acad. Sci. USA*, 86:7500-7504 (1989).

Colbert et al., "High-throughput screening for induced point mutations," *Plant Physiol.* 126:480-484 (2001).

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701 (1989).

Dehesh et al., "Overexpression of 3-ketoacyl-acyl-carrier protein synthase IIIs in plants reduces the rate of lipid synthesis," *Plant Physiol.*, 125:1103-1114 (2001).

Douglas et al., "Nutritional evaluation of low phytate and high protein corns," *Poultry Sci.* 79:1586-1591 (2000).

Eastmond et al., "Re-examining the role of the glyoxylate cycle in oilseeds," *Trends Plant Sci.*, 6:72-78 (2001).

Eccleston et al., "Expression of lauroyl-acyl carrier protein thioesterase in *Brassica napus* seeds induces pathways for both fatty acid oxidation and biosynthesis and implies a set point for triacylglycerol accumulation," *Plant Cell.* 10:613-622 (1998).

Edwards et al., "Protein and energy evaluation of soybean meals processed from genetically modified high-protein soybeans," *Poultry Sci.* 79:525-527 (1999).

Everett et al., "Genetic engineering of sunflower (*Helianthus annus* L.)," *Bio/technology*, 5:1201 (1987).

Falco et al., "Transgenic canola and soybean seeds with increased lysine," *Bio/Technology*, 13:577-582 (1995).

Fatland et al., "Molecular biology of cytosolic acetyl-CoA generation," *Biochem Soc Trans.*, 28:593-595 (2000).

Fatland et al., "Reverse genetic characterization of cytosolic acetyl-CoA generation by ATP-citrate lyase in *Arabidopsis*," *Plant Cell.*, 17:182-203 (2004).

(Continued)

*Primary Examiner*—Vinod Kumar
(74) *Attorney, Agent, or Firm*—Klarquist Sparkman, LLP

(57) ABSTRACT

The present invention is directed to plants that display an improved oil quantity phenotype or an improved meal quality phenotype due to altered expression of an HIO nucleic acid. The invention is further directed to methods of generating plants with an improved oil quantity phenotype or improved meal quality phenotype.

13 Claims, No Drawings

OTHER PUBLICATIONS

Feldmann et al., "A Dwarf Mutant of *Arabidopsis* Generated by T-DNA Insertion Mutagenesis," *Science*, 243:1351-1354 (1989).

Focks et al., "wrinkled1: A novel, low-seed-oil mutant of *Arabidopsis* with a deficiency in the seed-specific regulation of carbohydrate metabolism," *Plant Physiol.*, 118:91-101 (1998).

Fridborg et al., "The *Arabidopsis* dwarf mutant *shi* exhibits reduced gibberellin responses conferred by overexpression of a new putative zinc finger protein," *Plant Cell*, 11:1019-1032 (1999).

Girke et al., "Microarray analysis of developing *Arabidopsis* seeds," *Plant Physiol.* 124:1570-1581 (2000).

Hayashi et al., "Activation of a plant gene by T-DNA tagging: auxin-independent growth in vitro," *Science*, 258:1350-1353 (1992).

Honig and Rackis, "Determination of the total pepsin-pancreatin indigestible content (dietary fiber) of soybean products, wheat bran, and corn bran," *J. Agri. Food Chem.*, 27:1262-1266 (1979).

Jako et al., "Seed-specific over-expression of an *Arabidopsis* cDNA encoding a diacylglycerol acyltransferase enhances seed oil content and seed weight," *Plant Physiol.*, 126(2):861-74 (2001).

James and Dooner, "Isolation of EMS-induced mutants in *Arabidopsis* altered in seed fatty acid composition," *Theor. Appl. Genet.*, 80:241-245 (1990).

Kardailsky et al., "Activation tagging of the floral inducer FT," *Science*, 286:1962-1965 (1999).

Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409 (1995).

Katavic et al., "Utility of the *Arabidopsis* FAE1 and yeast SLC1-1 genes for improvements in erucic acid and oil content in rapeseed," *Biochem Soc Trans.*, 28:935-937 (2000).

Kline et al., "High velocity microprojectiles for delivering nucleic acids into living cells," *Nature*, 327:70-73 (1987).

Larson et al., "Acyl CoA profiles of transgenic plants that accumulate medium-chain fatty acids indicate inefficient storage lipid synthesis in developing oilseeds," *Plant J.*, 32:519-527 (2002).

Lemieux et al., "Mutants of *Arabidopsis* with alterations in seed lipid fatty acid composition," *Theor. Appl. Genet.*, 80:234-240 (1990).

Lin et al., "The Pex16p homolog SSE1 and storage organelle formation in *Arabidopsis* seeds," *Science*, 284:328-330 (1999).

Lionneton et al., "Development of an AFLP-based linkage map and localization of QTLs for seed fatty acid content in condiment mustard (*Brassica juncea*)," *Genome*, 45:1203-15 (2002).

Liu et al., "A transcriptional switch in the expression of yeast tricarboxylic acid cycle genes in response to a reduction or loss of respiratory function," *Mol Cell Biol.*, 19:6720-6728 (1999).

McCallum et al., "Targeted screening for induced mutations," *Nature Biotechnology*, 18:455-457 (2000).

Mekhedov et al., "Toward a functional catalog of the plant genome. A survey of genes for lipid biosynthesis," *Plant Physiol.*, 122:389-402 (2000).

Moire et al., "Impact of unusual fatty acid synthesis on futile cycling through beta-oxidation and on gene expression in transgenic plants," *Plant Physiol.*, 134:432-442 (2004).

Moore et al., "Chromatography of Amino Acids on Sulfonated Polystyrene Resins," *Anal. Chem.*, 30:1185-1190 (1958).

Mulder et al., "The InterPro Database, 2003 brings increased coverage and new features," *Nucleic Acids Res.*, 31:315-318, 2003.

Neuhaus et al., "Nonphotosynthetic Metabolism in Plastids," *Annu Rev Plant Physiol Plant Mol Biol.*, 51:111-140 (2000).

O'Hara et al., "Fatty acid and lipid biosynthetic genes are expressed at constant molar ratios but different absolute levels during embryogenesis," *Plant Physiol.*, 129:310-320 (2002).

Okuley et al., "*Arabidopsis* FAD2 gene encodes the enzyme that is essential for polyunsaturated lipid synthesis," *Plant Cell*, 6:147-158 (1994).

Parsons et al., "Nutritional evaluation of soybean meals varying in oligosaccharide content," *Poultry Sci.*, 79:1127-1131 (2000).

Pritchard et al., "Germination and storage reserve mobilization are regulated independently in *Arabidopsis*," *Plant J.*, 31:639-647 (2002).

Rangasamy et al., "Genetic enhancement of fatty acid synthesis by targeting rat liver ATP:citrate lyase into plastids of tobacco," *Plant Physiol.*, 122:1231-1238 (2000).

Rangasamy et al., "Compartmentation of ATP:citrate lyase in plants," *Plant Physiol.*, 122:1225-1230 (2000).

Ratledge et al., "Correlation of ATP/citrate lyase activity with lipid accumulation in developing seeds of *Brassica napus* L. Lipids," 32:7-12 (1997).

Rawsthorne, "Carbon flux and fatty acid synthesis in plants," *Prog Lipid Res*. 41:182-196 (2002).

Ruuska et al., "Contrapuntal networks of gene expression during *Arabidopsis* seed filling," *Plant Cell.*, 14:1191-1206 (2002).

Rylott et al., "Co-ordinate regulation of genes involved in storage lipid mobilization in *Arabidopsis thaliana*," *Biochem Soc Trans.*, 29:283-287 (2001).

Sakano et al., GenBank Accession No. AC034106, Aug. 3, 2000.

Schaffer et al., "The late elongated hypocotyl mutation of *Arabidopsis* disrupts circadian rhythms and the photoperiodic control of flowering," *Cell*, 93:1219-1229 (1998).

Schnarrenberger et al., "Evolution of the enzymes of the citric acid cycle and the glyoxylate cycle of higher plants. A case study of endosymbiotic gene transfer," *Eur J Biochem.*, 269:868-883 (2002).

Schnurr et al., "Characterization of an acyl-CoA synthetase from *Arabidopsis thaliana*," *Biochem Soc Trans.*, 28:957-958 (2000).

Shewry, "Seed storage proteins: structures and biosynthesis," *Plant Cell*, 7:945-956 (1995).

Shockey et al., "Characterization of the AMP-binding protein gene family in *Arabidopsis thaliana*: will the real acyl-CoA synthetases please stand up?" *Biochem Soc Trans.*, 28:955-957 (2000).

Thelen et al., "Biotin carboxyl carrier protein isoforms in Brassicaceae oilseeds," *Biochem Soc Trans.*, 28:595-598 (2000).

Weigel et al., "Activation tagging in *Arabidopsis*," *Plant Physiology*, 122:1003-1013 (2000).

White et al., "A new set of *Arabidopsis* expressed sequence tags from developing seeds. The metabolic pathway from carbohydrates to seed oil," *Plant Physiol.*, 124:1582-1594 (2000).

Wilson et al., "A Dissociation insertion causes a semidominant mutation that increases expression of TINY, an *Arabidopsis* gene related to APETALA2," *Plant Cell*, 8:659-671 (1996).

Yadav et al., "Cloning of higher plant omega-3 fatty acid desaturases," *Plant Physiol.*, 103:467-476 (1993).

* cited by examiner

```
                        SEQUENCE LISTING

<160> NUMBER OF SEQ ID NOS: 14

<210> SEQ ID NO 1
<211> LENGTH: 2755
<212> TYPE: DNA
<213> ORGANISM: Arabidopsis thaliana

<400> SEQUENCE: 1
agtctagaag aaccataatt acggattttg aaatttgggg attctatgag attcttcttc     60
ctctttggtt aaaaacctgg agattatcgt tttccaattc tagccttttc ttctcccctt    120
aatatcttct ctctgattct cttccgtttc gttttctcta ttccccgaga tcttttggtt    180
aaaggaagat aaagtttgaa acttttttat tgtttcacta ggcttgcgtt aatggcgaca    240
gttgtgtgat ggtccagagt tagcaagttt tacttactcg tttggttaaa aggacagaga    300
```

```
gtagagggaa aaaggctttg ttactgtttt ttttcgtctg cacattacta tggagtttct    360
cggcgacagt caaaatcacg atagctctga aacagagaag aagaacaaga agaagaagcg    420
atttcaccgt cacacacctc accagatcca acggcttgaa tcaactttca atgagtgtca    480
acatccagat gagaaacaga ggaaccaact tagtagagag ttgggtttag ctccaagaca    540
gatcaagttc tggtttcaaa acagaagaac tcaaaagaag gcacaacacg aaagagctga    600
taattgtgca ttgaaagaag agaatgataa gattcgatgc gaaaacattg ctattagaga    660
agctattaaa cacgccattt gccccagctg tggtgattct cctgttaatg aagactctta    720 cttttgatgag caaaagcttc gcatcgaaaa tgcacagctt agagatgagc tcgaaagggt    780
ttcgagtatt gcagctaaat tcttaggaag accaatctcc catcttccac cattactaaa    840
tccgatgcat gtttcgccat tagagttatt ccataccgga ccttcacttg attttgatct    900
tctcccagga agttgttctt caatgtctgt tccaagttta ccatctcagc caaacttggt    960
tttatcagag atggataagt ctcttatgac caacattgct gtgaccgcta tggaagaatt   1020
gcttaggctt cttcaaacaa atgagcctct gtggatcaaa actgatggat gcagagatgt   1080
tctcaatctc gaaaactatg agaatatgtt tacaagatca agtactagtg gtggaaagaa   1140
gaataacctt ggaatggaag catctagatc ttctggtgtt gttttcacta atgctattac   1200
acttgtggac atgcttatga actctgtcaa attaacagag cttttttccct cgatcgttgc   1260 atcatctaaa acccttgcag tgatttcatc gggattgcgt ggaaaccatg agatgcatt   1320 gcatttgatg attgaagagc ttcaagtgct ttcaccattg gtaacaacgc gtgagttctg   1380
tgtgctaaga tattgtcagc aaatcgaaca tggaacttgg gcaatagtaa atgtctcata   1440
tgagtttcct cagtttatat ctcaatctcg gtcatataga tttccttctg gttgcttgat   1500
ccaagatatg tccaatggct attcaaaggt tacttgggtg gaacatggtg aattcgagga   1560
gcaagaaccg atacatgaga tgtttaaaga tatagttcat aaaggattag cttttggagc   1620
tgaacgttgg attgctactc tccaaagaat gtgtgagaga ttcacgaatc tattggaacc   1680
tgcaacatca tcccttgatc ttggaggagt gattccatcg ccagaaggga agagaagtat   1740
aatgagactt gctcacagaa tggtaagcaa cttctgcttg agtgttggca catctaacaa   1800
cactcgctca acggttgtct cgggactgga tgaatttgga atccgtgtga cttcgcataa   1860
gagcagacat gaaccaaatg gaatggttct atgtgcagcc acaagtttct ggctccctat   1920
ttctccacaa aacgtcttca atttcctcaa agatgagaga actcggcctc agtgggacgt   1980
tctttcaaat ggaaactctg ttcaagaagt tgctcatatc acaaacggat caaatcctgg   2040
aaactgcata tctgttcttc gtggattcaa tgcatcatca tcacaaaaca acatgttgat   2100
tctacaagaa agctgcatag actcatcaag tgcagcgctt gtgatctaca ctccagtgga   2160
tctaccagcg ttgaacatag caatgagtgg tcaagacaca tcttatattc cgatattacc   2220
ctcaggtttt gccatttcac cagacggaag cagcaaagga ggaggatcat tgataacggt   2280
tgggtttcag ataatggtga gtggtttgca accggcaaaa ctgaacatgg agtcaatgga   2340
gacagtaaat aatctcatca ataccactgt ccaccaaatt aaaacgacct tgaattgtcc   2400
ttcaactgct tgagacgtca ttaaaagcta tttccccatc tgatttctga agggtctt   2460 caatgagcag agaagtgaaa gttattatta gtgttttgtc ttcaatgcct gcaaagagtg   2520
taagaaatca ttattcttct gggtatcact ctctctctcc tctttcttgt tctttattt    2580 tgagtttctt ttttaagctt agtgggaaag tgggagtcaa gaacgcacca tgcacaaatg   2640
tttttttgta tggttcgggc attgacttct gtttgtttgt tttttacttc tttttgtcta   2700
```
attacaatga ccaaattact atttcttctt ggtttaattt attccatagt ttctc   2755

<210> SEQ ID NO 2
<211> LENGTH: 687
<212> TYPE: PRT
<213> ORGANISM: Arabidopsis thaliana

<400> SEQUENCE: 2

| | | | | | | | | | | | | | | |
|---|---|---|---|---|---|---|---|---|---|---|---|---|---|---|
| Met | Glu | Phe | Leu | Gly | Asp | Ser | Gln | Asn | His | Asp | Ser | Glu | Thr | Glu |
| 1 | | | | 5 | | | | | 10 | | | | | 15 |
| Lys | Lys | Asn | Lys | Lys | Lys | Arg | Phe | His | Arg | His | Thr | Pro | His | Gln |
| | | | 20 | | | | | 25 | | | | | 30 | |
| Ile | Gln | Arg | Leu | Glu | Ser | Thr | Phe | Asn | Glu | Cys | Gln | His | Pro | Asp | Glu |
| | | | 35 | | | | 40 | | | | | 45 | | |
| Lys | Gln | Arg | Asn | Gln | Leu | Ser | Arg | Glu | Leu | Gly | Leu | Ala | Pro | Arg | Gln |
| | 50 | | | | | 55 | | | | | 60 | | | | |
| Ile | Lys | Phe | Trp | Phe | Gln | Asn | Arg | Arg | Thr | Gln | Lys | Lys | Ala | Gln | His |
| 65 | | | | | 70 | | | | | 75 | | | | | 80 |
| Glu | Arg | Ala | Asp | Asn | Cys | Ala | Leu | Lys | Glu | Glu | Asn | Asp | Lys | Ile | Arg |
| | | | | 85 | | | | | 90 | | | | | 95 | |
| Cys | Glu | Asn | Ile | Ala | Ile | Arg | Glu | Ala | Ile | Lys | His | Ala | Ile | Cys | Pro |
| | | | 100 | | | | | 105 | | | | | 110 | | |
| Ser | Cys | Gly | Asp | Ser | Pro | Val | Asn | Glu | Asp | Ser | Tyr | Phe | Asp | Glu | Gln |
| | | | 115 | | | | 120 | | | | | 125 | | | |
| Lys | Leu | Arg | Ile | Glu | Asn | Ala | Gln | Leu | Arg | Asp | Glu | Leu | Glu | Arg | Val |
| | 130 | | | | | 135 | | | | | 140 | | | | |
| Ser | Ser | Ile | Ala | Ala | Lys | Phe | Leu | Gly | Arg | Pro | Ile | Ser | His | Leu | Pro |
| 145 | | | | | 150 | | | | | 155 | | | | | 160 |
| Pro | Leu | Leu | Asn | Pro | Met | His | Val | Ser | Pro | Leu | Glu | Leu | Phe | His | Thr |
| | | | | 165 | | | | | 170 | | | | | 175 | |
| Gly | Pro | Ser | Leu | Asp | Phe | Asp | Leu | Leu | Pro | Gly | Ser | Cys | Ser | Ser | Met |
| | | | 180 | | | | | 185 | | | | | 190 | | |
| Ser | Val | Pro | Ser | Leu | Pro | Ser | Gln | Pro | Asn | Leu | Val | Leu | Ser | Glu | Met |
| | | | 195 | | | | | 200 | | | | | 205 | | |
| Asp | Lys | Ser | Leu | Met | Thr | Asn | Ile | Ala | Val | Thr | Ala | Met | Glu | Glu | Leu |
| | 210 | | | | | 215 | | | | | 220 | | | | |
| Leu | Arg | Leu | Leu | Gln | Thr | Asn | Glu | Pro | Leu | Trp | Ile | Lys | Thr | Asp | Gly |
| 225 | | | | | 230 | | | | | 235 | | | | | 240 |
| Cys | Arg | Asp | Val | Leu | Asn | Leu | Glu | Asn | Tyr | Glu | Asn | Met | Phe | Thr | Arg |
| | | | | 245 | | | | | 250 | | | | | 255 | |
| Ser | Ser | Thr | Ser | Gly | Gly | Lys | Lys | Asn | Asn | Leu | Gly | Met | Glu | Ala | Ser |
| | | | 260 | | | | | 265 | | | | | 270 | | |
| Arg | Ser | Ser | Gly | Val | Val | Phe | Thr | Asn | Ala | Ile | Thr | Leu | Val | Asp | Met |
| | | | 275 | | | | | 280 | | | | | 285 | | |
| Leu | Met | Asn | Ser | Val | Lys | Leu | Thr | Glu | Leu | Phe | Pro | Ser | Ile | Val | Ala |
| | 290 | | | | | 295 | | | | | 300 | | | | |
| Ser | Ser | Lys | Thr | Leu | Ala | Val | Ile | Ser | Ser | Gly | Leu | Arg | Gly | Asn | His |
| 305 | | | | | 310 | | | | | 315 | | | | | 320 |
| Gly | Asp | Ala | Leu | His | Leu | Met | Ile | Glu | Glu | Leu | Gln | Val | Leu | Ser | Pro |
| | | | | 325 | | | | | 330 | | | | | 335 | |
| Leu | Val | Thr | Thr | Arg | Glu | Phe | Cys | Val | Leu | Arg | Tyr | Cys | Gln | Gln | Ile |
| | | | 340 | | | | | 345 | | | | | 350 | | |
| Glu | His | Gly | Thr | Trp | Ala | Ile | Val | Asn | Val | Ser | Tyr | Glu | Phe | Pro | Gln |
| | | | 355 | | | | | 360 | | | | | 365 | | |

```
Phe Ile Ser Gln Ser Arg Ser Tyr Arg Phe Pro Ser Gly Cys Leu Ile
    370                 375                 380

Gln Asp Met Ser Asn Gly Tyr Ser Lys Val Thr Trp Val Glu His Gly
385                 390                 395                 400

Glu Phe Glu Glu Gln Glu Pro Ile His Glu Met Phe Lys Asp Ile Val
                405                 410                 415

His Lys Gly Leu Ala Phe Gly Ala Glu Arg Trp Ile Ala Thr Leu Gln
            420                 425                 430

Arg Met Cys Glu Arg Phe Thr Asn Leu Leu Glu Pro Ala Thr Ser Ser
        435                 440                 445

Leu Asp Leu Gly Gly Val Ile Pro Ser Pro Glu Gly Lys Arg Ser Ile
    450                 455                 460

Met Arg Leu Ala His Arg Met Val Ser Asn Phe Cys Leu Ser Val Gly
465                 470                 475                 480

Thr Ser Asn Asn Thr Arg Ser Thr Val Val Ser Gly Leu Asp Glu Phe
                485                 490                 495

Gly Ile Arg Val Thr Ser His Lys Ser Arg His Glu Pro Asn Gly Met
            500                 505                 510

Val Leu Cys Ala Ala Thr Ser Phe Trp Leu Pro Ile Ser Pro Gln Asn
        515                 520                 525

Val Phe Asn Phe Leu Lys Asp Glu Arg Thr Arg Pro Gln Trp Asp Val
    530                 535                 540

Leu Ser Asn Gly Asn Ser Val Gln Glu Val Ala His Ile Thr Asn Gly
545                 550                 555                 560

Ser Asn Pro Gly Asn Cys Ile Ser Val Leu Arg Gly Phe Asn Ala Ser
                565                 570                 575

Ser Ser Gln Asn Asn Met Leu Ile Leu Gln Glu Ser Cys Ile Asp Ser
            580                 585                 590

Ser Ser Ala Ala Leu Val Ile Tyr Thr Pro Val Asp Leu Pro Ala Leu
        595                 600                 605

Asn Ile Ala Met Ser Gly Gln Asp Thr Ser Tyr Ile Pro Ile Leu Pro
    610                 615                 620

Ser Gly Phe Ala Ile Ser Pro Asp Gly Ser Ser Lys Gly Gly Gly Ser
625                 630                 635                 640

Leu Ile Thr Val Gly Phe Gln Ile Met Val Ser Gly Leu Gln Pro Ala
                645                 650                 655

Lys Leu Asn Met Glu Ser Met Glu Thr Val Asn Asn Leu Ile Asn Thr
            660                 665                 670

Thr Val His Gln Ile Lys Thr Thr Leu Asn Cys Pro Ser Thr Ala
        675                 680                 685

<210> SEQ ID NO 3
<211> LENGTH: 1831
<212> TYPE: DNA
<213> ORGANISM: Arabidopsis thaliana

<400> SEQUENCE: 3
cctcgagaac aaaaaaaact tctttttttt tctctttctc tcttggcttc tctttagaaa    60
gtgactcacc agaaaaaaaa aagggttttt gcttttcggg tttagctaag aaaaatcttt   120
caatcttcct taaatctttc aaaaccccaa aatgggacct cgttgctcta agctctctct   180
ctgttggtgg ccgacccatc tcaaatcaac tcaaacgaa gcttctgatc tagataacgg    240
aacggacgat tgccgtcgt ttacggagtt tagtttcgac caactacgag ctgctacttg    300
```

-continued

```
tggattctct acagacagta ttgtctccga catggtgtt aaagctccta atgttgtgta      360
taaaggcaga cttgaagatg accgatggat cgctgttaaa cgattcaata gatccgcttg      420
gcctgatact cgtcaatttc ttgaagaagc aaaagctgtg gggcagttga ggaatgagag      480
gttggcgaat ttgattggat ctgttgtga aggagacgag agattgctcg ttgctgagtt      540
tatgccttt gaaactctct cgaagcatct ctttcactgg gatagtcagc caatgaagtg      600
gtctatgagg ttgagagtgg ctttgtatct tgcacaagca cttgagtatt gtagcagcaa      660
aggtcgcgcc ttgtaccacg atcttaatgc ttacaggatc ttgtttgacc aggatggtaa      720
cccgagatta tcttgctttg gtcttatgaa gaatagtagg gatgggaaga gttacagtac      780
aaatttggct ttcacacctc ctgaatacct aagaacaggg agagtgattc cggagagtgt      840
ggtctacagc ttcggaacgc tgttgctaga tcttctcagc ggcaaacaca taccaccaag      900
ccatgcgctt gatctgattc gtgggaagaa tttcctgatg ctgatggact cgtgtctaga      960
tggccatttc tcaaacgatg atggaaccga ttggttcgt ttagcttccc gttgtttgca     1020
gtatgaagct cgtgaaaggc aaatgtgaa atctctcgtg cctcactcg ctcctcttca     1080
gaaagaaact gatattccgt ctcatgtttt aatggggatt ccacatggag ctgcttctcc     1140
aaaggaaaca acttcgctta cccctcttgg tgacgcttgt tcacgacatg atctcacagc     1200
aatacatgaa attctcgaaa aggttggata caaagatgac gagggtgtag caatgagct     1260
ctcgttccaa gtgtggaccg accagattca ggagactcta aactccaaga acaaggaga     1320
tgctgcgttc aaaggcaaag actttgtcac tgctgttgaa tgttacacgc agttcatcga     1380
agatggcaca atggtatcgc caacagtttt tgcaaggagg tgtttgtgtt atctgatgag     1440
caatatgcct caagaggctc ttggtgatgc aatgcaggcg caagtagtgt ctcctgaatg     1500
gccaacggct ttctatcttc aggccgctgc tctcttcagc cttggaatgg ataaagacgc     1560
ctgtgaaacc ctaaaagatg gaacttcctt ggaagccaag aaacataaca acagaaactg     1620
aaaacttcaa gtgtataggt ttcttctctc ttccgccttc ttcgttttgt gattggattc     1680
tgagaaagcc tcattgtctc tgtcttcttt aagcattatc ttaaatttgt ggtttccaat     1740
ttgaagagat gattcaaatc acatttgaat caagaaaaga aggatctttc tcatttaagt     1800
ccaagatcct tatatgagat tgttcaaac t                                     1831
```

<210> SEQ ID NO 4
<211> LENGTH: 489
<212> TYPE: PRT
<213> ORGANISM: Arabidopsis thaliana

<400> SEQUENCE: 4

```
Met Gly Pro Arg Cys Ser Lys Leu Ser Leu Cys Trp Trp Pro Thr His
1               5                  10                  15

Leu Lys Ser Thr His Asn Glu Ala Ser Asp Leu Asp Asn Gly Thr Asp
            20                  25                  30

Asp Leu Pro Ser Phe Thr Glu Phe Ser Phe Asp Gln Leu Arg Ala Ala
        35                  40                  45

Thr Cys Gly Phe Ser Thr Asp Ser Ile Val Ser Glu His Gly Val Lys
    50                  55                  60

Ala Pro Asn Val Val Tyr Lys Gly Arg Leu Glu Asp Asp Arg Trp Ile
65                  70                  75                  80

Ala Val Lys Arg Phe Asn Arg Ser Ala Trp Pro Asp Thr Arg Gln Phe
                85                  90                  95

Leu Glu Glu Ala Lys Ala Val Gly Gln Leu Arg Asn Glu Arg Leu Ala
```

-continued

```
                    100                 105                 110
Asn Leu Ile Gly Phe Cys Cys Glu Gly Asp Glu Arg Leu Leu Val Ala
            115                 120                 125
Glu Phe Met Pro Phe Glu Thr Leu Ser Lys His Leu Phe His Trp Asp
130                 135                 140
Ser Gln Pro Met Lys Trp Ser Met Arg Leu Arg Val Ala Leu Tyr Leu
145                 150                 155                 160
Ala Gln Ala Leu Glu Tyr Cys Ser Ser Lys Gly Arg Ala Leu Tyr His
                165                 170                 175
Asp Leu Asn Ala Tyr Arg Ile Leu Phe Asp Gln Asp Gly Asn Pro Arg
            180                 185                 190
Leu Ser Cys Phe Gly Leu Met Lys Asn Ser Arg Asp Gly Lys Ser Tyr
        195                 200                 205
Ser Thr Asn Leu Ala Phe Thr Pro Pro Glu Tyr Leu Arg Thr Gly Arg
    210                 215                 220
Val Ile Pro Glu Ser Val Val Tyr Ser Phe Gly Thr Leu Leu Leu Asp
225                 230                 235                 240
Leu Leu Ser Gly Lys His Ile Pro Pro Ser His Ala Leu Asp Leu Ile
                245                 250                 255
Arg Gly Lys Asn Phe Leu Met Leu Met Asp Ser Cys Leu Asp Gly His
            260                 265                 270
Phe Ser Asn Asp Asp Gly Thr Asp Leu Val Arg Leu Ala Ser Arg Cys
        275                 280                 285
Leu Gln Tyr Glu Ala Arg Glu Arg Pro Asn Val Lys Ser Leu Val Ser
    290                 295                 300
Ser Leu Ala Pro Leu Gln Lys Glu Thr Asp Ile Pro Ser His Val Leu
305                 310                 315                 320
Met Gly Ile Pro His Gly Ala Ala Ser Pro Lys Glu Thr Thr Ser Leu
                325                 330                 335
Thr Pro Leu Gly Asp Ala Cys Ser Arg His Asp Leu Thr Ala Ile His
            340                 345                 350
Glu Ile Leu Glu Lys Val Gly Tyr Lys Asp Asp Glu Gly Val Ala Asn
        355                 360                 365
Glu Leu Ser Phe Gln Val Trp Thr Asp Gln Ile Gln Glu Thr Leu Asn
    370                 375                 380
Ser Lys Lys Gln Gly Asp Ala Ala Phe Lys Gly Lys Asp Phe Val Thr
385                 390                 395                 400
Ala Val Glu Cys Tyr Thr Gln Phe Ile Glu Asp Gly Thr Met Val Ser
                405                 410                 415
Pro Thr Val Phe Ala Arg Arg Cys Leu Cys Tyr Leu Met Ser Asn Met
            420                 425                 430
Pro Gln Glu Ala Leu Gly Asp Ala Met Gln Ala Gln Val Val Ser Pro
        435                 440                 445
Glu Trp Pro Thr Ala Phe Tyr Leu Gln Ala Ala Leu Phe Ser Leu
    450                 455                 460
Gly Met Asp Lys Asp Ala Cys Glu Thr Leu Lys Asp Gly Thr Ser Leu
465                 470                 475                 480
Glu Ala Lys Lys His Asn Asn Arg Asn
                485

<210> SEQ ID NO 5
<211> LENGTH: 3201
<212> TYPE: DNA
<213> ORGANISM: Arabidopsis thaliana
```

<400> SEQUENCE: 5

```
acgatcttcg atccagagtt gagcttctct tctgccatcg tcttcttcct cgatctcggt      60
caattacgca ttctctgatc tgatttgtga gatctctcgt cggatcaccg ttttttacat     120
cgtcgccgac aacacttagg agtaattgga tccagcagaa atgtcgataa acatgaaaac     180
atttactcaa gctctagcta gaacggctgc tgtgattgag aagacggttc ataccacagt     240
acaggaagtt acgggaccaa aggctcttca ggattacgag ctacttgatc agatcggttc     300
cgctggtcct ggtctagctt ggaagctata cgcagctaag gcgcgtgatt ccacgaggcc     360
acagcagtac ccgacggtct gtgtatggat gcttgataag cgtgctttgt cggaggctcg     420
tgtacgagcg aatttgtcta aggcagctga agatgcgttt cttgatctga ttcgagctga     480
tgcggggaag ctggtgaggt tgaggcatcc tggtgtggtt catgtggtgc aagcgcttga     540
tgagaataag aatgctatgg ctttagttac ggagccgctt tttgcttctg tggctaatgc     600
gcttggtaat gttgagaatg tgggtaatgt gccgaaagat ctgaaatcaa tggagatgag     660
cttgttggag gtgaagcatg gtctgctcca gatttctgag acactgaact tcttacacaa     720
taacgcaaat ctcatccatc gagccatttc tccagagaat gttcttatta cttcagctgg     780
ttcttggaag cttgccgggt ttggttttgc tatttcagca gcacaggctg ggaatttgga     840
taacatgcaa tcgttccact attctgaata cgacgtcgag gattcaatac tgccagtcca     900
gccatctcta aattacactg cacctgaact gatgcgcagc aaaagtcctt cagctggagc     960
ttcgtcggac attttagtt ttggatgcct tgcctatcat ttagttgctc ggaaaccgtt    1020
gtttgactgc aataataatg tcaagatgta catgaacacg ttgaactata taacaaatga    1080
atctttctca tctataccct cggaattggt atctgatttg caaggatgc tatcaacgaa    1140
cgagtccttt agaccaacag cattagattt cacaggatcg aatttttttcc gaagtgacgc    1200
taggttacgt gctctccgct tccttgatca tttgcttgaa agagataaca tgcaaaagtc    1260
cgagttctta aaagcattat cagatatgtg gaaagatttt gattcccgtg tattacggta    1320
taaggtgctt ccacctcttt gtgcggaact taggaattta gttttgcaac caataatctt    1380
gccaatggtt ctaactatag cacagtctca ggatagaact gactttgagc tgataacact    1440
tccggctctt gttcctgttc tgagtactgc ttcaggagat acattactgc tgcttgtgaa    1500
acatgcagat cttattacta caagactga tagtgagcat cttgtatcgc acgtcctccc    1560
tttgcttctg cgagcctaca atgataacga tgtccgcatt caggaggaag ttcttaaaag    1620
atccacatct gtggctaagc aactcgatgg tcaggttgtg aggcaagcaa ttttgcctcg    1680
tgttcatggc ttggctctca aaactacagt tgctgcggtc agagtaaatg ctttgctctg    1740
cttagctgag ttggtgcaaa cgcttgataa gcctgccgct atcgaaattc tggaaacaat    1800
tcaacggtgt actgccgtag atcgttctgc accaaccccta atgtgtaccc ttgctgtggc    1860
aaacgcaatc ctcaaacagt atggagttga attcacagca gaacatgtgc ttaccctgat    1920
gatgccgctt ctcactgccc aacaactgaa cgtccaacag tttgccaaat atatgctatt    1980
tgtcaaggat attctcagga aaatagagga aaaagagga gtaacagtga acgattccgg    2040
agtcccagag gtgaaaccgc attctgctgc caatggactc cagtttcagt catcaaccca    2100
aatacctgag aaggttgctt ctgcagccaa gagcagtcct gcatgggatg aagattgggg    2160
ctcccccgagc aaagattctg ctgtgggaaa tcctgcttct tctcgtcata acacaaacga    2220
tcagtttaac aaatccacag atcagtcaca gccatcgatc atgtctactc tgcccaacaa    2280
```

-continued

```
gacaacagcg ccaacaacat gccctgcagt ggacatcgag tggcctccaa ggcaatcttc      2340
aagcctcact gctccagcaa ctgataatca gacacaacta aacacaggaa catcatttgc      2400
ttcgggtttc gatgagttag atccgtttgc taattggcct ccacgtccca acaatggtgc      2460
ttctgttgct tctactggtc tcaagaatgg cgctgcatcc aattttagca acaatttacc      2520
aggcggcacc cattttcaga cagctaacaa tgacaactgg gcattcagca gtgcctcctt      2580
gtcttcgcta aaaccacccc agcaagggaa tcaaggtatc tctgcaaata atcaagatcc      2640
actcaactct ttcggtgtac caaaacagag ccaaggaatg ccatctttca ccagtggttc      2700
atacaacaac cagaagccag cagacatcag ttccatattc ggttcaagca aaaccgaacc      2760
gtccgcaatg aaactcgcac caccaccttc aatagcaatg ggaagaggaa ggggtagagg      2820
tagaggtggt actggcacat ctacctcaaa gcccagtggt tcacaaccat ctctattgga      2880
tctattatga ccacagttct tggtgttgaa cctcttggtg tggtgttggt gttttgtcgt      2940
gtgattaaga gaagcatata cacatggaga ttgcgctccg tgctttgtga tgcagagaaa      3000
actgttcaga aaaatggaga tgttatgtaa acatcttctg ggattagctt cttccactat      3060
ataaacttta ctacagcttc aggttgtttt atgtctttct caaattgtac aaattttgtt      3120
atgttttctc accattgctt catttgtcac acataatatt attttacggc ggctacgcta      3180
ttttcatgta tacttttct t                                                3201
```

<210> SEQ ID NO 6
<211> LENGTH: 909
<212> TYPE: PRT
<213> ORGANISM: Arabidopsis thaliana

<400> SEQUENCE: 6

```
Met Ser Ile Asn Met Lys Thr Phe Thr Gln Ala Leu Ala Arg Thr Ala
1               5                   10                  15

Ala Val Ile Glu Lys Thr Val His Thr Thr Val Gln Glu Val Thr Gly
            20                  25                  30

Pro Lys Ala Leu Gln Asp Tyr Glu Leu Leu Asp Gln Ile Gly Ser Ala
        35                  40                  45

Gly Pro Gly Leu Ala Trp Lys Leu Tyr Ala Ala Lys Ala Arg Asp Ser
    50                  55                  60

Thr Arg Pro Gln Gln Tyr Pro Thr Val Cys Val Trp Met Leu Asp Lys
65                  70                  75                  80

Arg Ala Leu Ser Glu Ala Arg Val Arg Ala Asn Leu Ser Lys Ala Ala
                85                  90                  95

Glu Asp Ala Phe Leu Asp Leu Ile Arg Ala Asp Ala Gly Lys Leu Val
            100                 105                 110

Arg Leu Arg His Pro Gly Val Val His Val Val Gln Ala Leu Asp Glu
        115                 120                 125

Asn Lys Asn Ala Met Ala Leu Val Thr Glu Pro Leu Phe Ala Ser Val
    130                 135                 140

Ala Asn Ala Leu Gly Asn Val Glu Asn Val Gly Asn Val Pro Lys Asp
145                 150                 155                 160

Leu Lys Ser Met Glu Met Ser Leu Leu Glu Val Lys His Gly Leu Leu
                165                 170                 175

Gln Ile Ser Glu Thr Leu Asn Phe Leu His Asn Ala Asn Leu Ile
            180                 185                 190

His Arg Ala Ile Ser Pro Glu Asn Val Leu Ile Thr Ser Ala Gly Ser
        195                 200                 205
```

-continued

```
Trp Lys Leu Ala Gly Phe Gly Phe Ala Ile Ser Ala Ala Gln Ala Gly
    210                 215                 220
Asn Leu Asp Asn Met Gln Ser Phe His Tyr Ser Glu Tyr Asp Val Glu
225                 230                 235                 240
Asp Ser Ile Leu Pro Val Gln Pro Ser Leu Asn Tyr Thr Ala Pro Glu
                245                 250                 255
Leu Met Arg Ser Lys Ser Pro Ser Ala Gly Ala Ser Ser Asp Ile Phe
            260                 265                 270
Ser Phe Gly Cys Leu Ala Tyr His Leu Val Ala Arg Lys Pro Leu Phe
        275                 280                 285
Asp Cys Asn Asn Val Lys Met Tyr Met Asn Thr Leu Asn Tyr Ile
    290                 295                 300
Thr Asn Glu Ser Phe Ser Ser Ile Pro Ser Glu Leu Val Ser Asp Leu
305                 310                 315                 320
Gln Arg Met Leu Ser Thr Asn Glu Ser Phe Arg Pro Thr Ala Leu Asp
                325                 330                 335
Phe Thr Gly Ser Asn Phe Phe Arg Ser Asp Ala Arg Leu Arg Ala Leu
            340                 345                 350
Arg Phe Leu Asp His Leu Leu Glu Arg Asp Asn Met Gln Lys Ser Glu
        355                 360                 365
Phe Leu Lys Ala Leu Ser Asp Met Trp Lys Asp Phe Asp Ser Arg Val
    370                 375                 380
Leu Arg Tyr Lys Val Leu Pro Pro Leu Cys Ala Glu Leu Arg Asn Leu
385                 390                 395                 400
Val Leu Gln Pro Ile Ile Leu Pro Met Val Leu Thr Ile Ala Gln Ser
                405                 410                 415
Gln Asp Arg Thr Asp Phe Glu Leu Ile Thr Leu Pro Ala Leu Val Pro
            420                 425                 430
Val Leu Ser Thr Ala Ser Gly Asp Thr Leu Leu Leu Val Lys His
        435                 440                 445
Ala Asp Leu Ile Thr Asn Lys Thr Asp Ser Glu His Leu Val Ser His
    450                 455                 460
Val Leu Pro Leu Leu Arg Ala Tyr Asn Asp Asn Asp Val Arg Ile
465                 470                 475                 480
Gln Glu Glu Val Leu Lys Arg Ser Thr Ser Val Ala Lys Gln Leu Asp
                485                 490                 495
Gly Gln Val Val Arg Gln Ala Ile Leu Pro Arg Val His Gly Leu Ala
            500                 505                 510
Leu Lys Thr Thr Val Ala Ala Val Arg Val Asn Ala Leu Leu Cys Leu
        515                 520                 525
Ala Glu Leu Val Gln Thr Leu Asp Lys Pro Ala Ala Ile Glu Ile Leu
    530                 535                 540
Glu Thr Ile Gln Arg Cys Thr Ala Val Asp Arg Ser Ala Pro Thr Leu
545                 550                 555                 560
Met Cys Thr Leu Ala Val Ala Asn Ala Ile Leu Lys Gln Tyr Gly Val
                565                 570                 575
Glu Phe Thr Ala Glu His Val Leu Leu Met Met Pro Leu Leu Thr
            580                 585                 590
Ala Gln Gln Leu Asn Val Gln Gln Phe Ala Lys Tyr Met Leu Phe Val
        595                 600                 605
Lys Asp Ile Leu Arg Lys Ile Glu Glu Lys Arg Gly Val Thr Val Asn
    610                 615                 620
Asp Ser Gly Val Pro Glu Val Lys Pro His Ser Ala Ala Asn Gly Leu
```

-continued

```
        625                 630                 635                 640
Gln Phe Gln Ser Ser Thr Gln Ile Pro Glu Lys Val Ala Ser Ala Ala
                    645                 650                 655
Lys Ser Ser Pro Ala Trp Asp Glu Asp Trp Gly Ser Pro Ser Lys Asp
                660                 665                 670
Ser Ala Val Gly Asn Pro Ala Ser Ser Arg His Asn Thr Asn Asp Gln
            675                 680                 685
Phe Asn Lys Ser Thr Asp Gln Ser Gln Pro Ser Ile Met Ser Thr Leu
        690                 695                 700
Pro Asn Lys Thr Thr Ala Pro Thr Thr Cys Pro Ala Val Asp Ile Glu
705                 710                 715                 720
Trp Pro Pro Arg Gln Ser Ser Leu Thr Ala Pro Ala Thr Asp Asn
                725                 730                 735
Gln Thr Gln Leu Asn Thr Gly Thr Ser Phe Ala Ser Gly Phe Asp Glu
                740                 745                 750
Leu Asp Pro Phe Ala Asn Trp Pro Pro Arg Pro Asn Asn Gly Ala Ser
                755                 760                 765
Val Ala Ser Thr Gly Leu Lys Asn Gly Ala Ala Ser Asn Phe Ser Asn
        770                 775                 780
Asn Leu Pro Gly Gly Thr His Phe Gln Thr Ala Asn Asn Asp Asn Trp
785                 790                 795                 800
Ala Phe Ser Ser Ala Ser Leu Ser Ser Leu Lys Pro Pro Gln Gln Gly
                805                 810                 815
Asn Gln Gly Ile Ser Ala Asn Asn Gln Asp Pro Leu Asn Ser Phe Gly
            820                 825                 830
Val Pro Lys Gln Ser Gln Gly Met Pro Ser Phe Thr Ser Gly Ser Tyr
        835                 840                 845
Asn Asn Gln Lys Pro Ala Asp Ile Ser Ser Ile Phe Gly Ser Ser Lys
    850                 855                 860
Thr Glu Pro Ser Ala Met Lys Leu Ala Pro Pro Ser Ile Ala Met
865                 870                 875                 880
Gly Arg Gly Arg Gly Arg Gly Arg Gly Thr Gly Thr Ser Thr Ser
                885                 890                 895
Lys Pro Ser Gly Ser Gln Pro Ser Leu Leu Asp Leu Leu
        900                 905

<210> SEQ ID NO 7
<211> LENGTH: 1694
<212> TYPE: DNA
<213> ORGANISM: Arabidopsis thaliana

<400> SEQUENCE: 7
gtggaacagt ggcttgtggc ttgattaatc ggaaacttga aagcttcctc ctgaaggaat    60
ttagaaagcg tgagagatgg cgacgaagac tgtttggatc atactgttgt gtctatttgt   120
tgtttcccag gcagatcagg gtttcgatgt tcgtcatcac ctctccaccg tcaccagata   180
ctctacttcg aaagatgtta cccaaaattt gattgaaggg tcgaatgttc ctagtgagtg   240
tacacctatc caccttaacc ttgtggctag catggaact cgttctccga ccaagaaacg    300
attgcgggaa ttgaaagtt tggctggtag gtttaaggaa ctggtaagag atgcagaagc    360
taggaaattg ccttcagaca aaattcctgg atggttggga caatggaaat ctccttggga   420
aggaaaagtg aaaggtgggg agctgatcag gcaggggag gatgagtat accaactggg     480 aattcgggt cgggaacggt ttcctagttt gtttgaagag gattaccatc ctgatgtcta    540
```

-continued

```
tacaataaga gctacgcaga ttcctagggc atctgcaagt gctgtagcat ttggaatggg      600
gttattcagt gagaaaggaa atctgggacc aggccgtaat agagcattcg ctgtcactag      660
cgaaaaccgt gccagtgata caaagttgag attttttgaa tgttgtcaaa actacaagag      720
ctatagaaaa gctaaagagc ctgctgtgga taagctcaag gaacctgttc tgaataaaat      780
tacagcttcc gttgcaaaga gatatgattt aaaattcacg aaacaggaca tttcttctct      840
ctggtttctg tgcaagcagg aagcatcatt gcttaatgta actaatcaaa gttgtgaact      900
tttcacgcca tcagaggttg ctttgctgga atggacagat gatttggaag tgtttctcct      960
caaaggttat ggaaattcct tgaattacaa aatgggagtt ccacttctag aagatgtttt     1020
gcattcaatg aagaagcta tcaaggcccg ggaagaaaag ctcccacctg aagttacga       1080 aaaagcaagg cttaggtttg cacatgccga acaatagtt ccctttcctt gtcttcttgg      1140
gcttttcctt gatggatctg agtttgagaa aatacagaag gagaaacctt tggaactccc     1200
tccacagcct cccaaaacca gggattttag aggcagcacc atggctcctt ttggtgggaa     1260
caacattctt gtcctataca gttgtcccgc agaatcctct cccaaatact cgttcaggt      1320 tctgcacaat gagcatccta ttgcagtgcc aggttgtgat ggaaaagatt tctgtcctct     1380
tgaagatttc aaggccaaag tggtaactcc tcatctaaag catgcttttg acaacctttg     1440
caatgctgat ctaaatgacc tgaaacagaa gcctgcatca agtaagttat ctatactgtc     1500
aagttggctg tttgggtcaa gccacgatac cgagctctag ttactacaca gctcttctta     1560
catactggct gattacagtt tgaacctgaa atcacacaga gcattgttgt ctgtttttt      1620 ttttgtcccc ttgccacatt tgtgttctag ttagttcaat ccgctaatct gaaatatttt     1680
gattttgatc tctg                                                       1694
```

<210> SEQ ID NO 8
<211> LENGTH: 487
<212> TYPE: PRT
<213> ORGANISM: Arabidopsis thaliana

<400> SEQUENCE: 8

```
Met Ala Thr Lys Thr Val Trp Ile Ile Leu Leu Cys Leu Phe Val Val
1               5                   10                  15

Ser Gln Ala Asp Gln Gly Phe Asp Val Arg His His Leu Ser Thr Val
            20                  25                  30

Thr Arg Tyr Ser Thr Ser Lys Asp Val Thr Gln Asn Leu Ile Glu Gly
        35                  40                  45

Ser Asn Val Pro Ser Glu Cys Thr Pro Ile His Leu Asn Leu Val Ala
    50                  55                  60

Arg His Gly Thr Arg Ser Pro Thr Lys Lys Arg Leu Arg Glu Leu Glu
65                  70                  75                  80

Ser Leu Ala Gly Arg Phe Lys Glu Leu Val Arg Asp Ala Glu Ala Arg
                85                  90                  95

Lys Leu Pro Ser Asp Lys Ile Pro Gly Trp Leu Gly Gln Trp Lys Ser
            100                 105                 110

Pro Trp Glu Gly Lys Val Lys Gly Gly Glu Leu Ile Arg Gln Gly Glu
        115                 120                 125

Asp Glu Leu Tyr Gln Leu Gly Ile Arg Val Arg Glu Arg Phe Pro Ser
    130                 135                 140

Leu Phe Glu Glu Asp Tyr His Pro Asp Val Tyr Thr Ile Arg Ala Thr
145                 150                 155                 160

Gln Ile Pro Arg Ala Ser Ala Ser Ala Val Ala Phe Gly Met Gly Leu
```

```
                165                 170                 175
Phe Ser Glu Lys Gly Asn Leu Gly Pro Gly Arg Asn Arg Ala Phe Ala
            180                 185                 190
Val Thr Ser Glu Asn Arg Ala Ser Asp Thr Lys Leu Arg Phe Phe Glu
            195                 200                 205
Cys Cys Gln Asn Tyr Lys Ser Tyr Arg Lys Ala Lys Glu Pro Ala Val
            210                 215                 220
Asp Lys Leu Lys Glu Pro Val Leu Asn Lys Ile Thr Ala Ser Val Ala
225                 230                 235                 240
Lys Arg Tyr Asp Leu Lys Phe Thr Lys Gln Asp Ile Ser Ser Leu Trp
                245                 250                 255
Phe Leu Cys Lys Gln Glu Ala Ser Leu Leu Asn Val Thr Asn Gln Ser
            260                 265                 270
Cys Glu Leu Phe Thr Pro Ser Glu Val Ala Leu Leu Glu Trp Thr Asp
            275                 280                 285
Asp Leu Glu Val Phe Leu Leu Lys Gly Tyr Gly Asn Ser Leu Asn Tyr
            290                 295                 300
Lys Met Gly Val Pro Leu Leu Glu Asp Val Leu His Ser Met Glu Glu
305                 310                 315                 320
Ala Ile Lys Ala Arg Glu Lys Leu Pro Pro Gly Ser Tyr Glu Lys
                325                 330                 335
Ala Arg Leu Arg Phe Ala His Ala Glu Thr Ile Val Pro Phe Ser Cys
            340                 345                 350
Leu Leu Gly Leu Phe Leu Asp Gly Ser Glu Phe Glu Lys Ile Gln Lys
            355                 360                 365
Glu Lys Pro Leu Glu Leu Pro Pro Gln Pro Pro Lys Thr Arg Asp Phe
            370                 375                 380
Arg Gly Ser Thr Met Ala Pro Phe Gly Gly Asn Asn Ile Leu Val Leu
385                 390                 395                 400
Tyr Ser Cys Pro Ala Glu Ser Ser Pro Lys Tyr Phe Val Gln Val Leu
                405                 410                 415
His Asn Glu His Pro Ile Ala Val Pro Gly Cys Asp Gly Lys Asp Phe
            420                 425                 430
Cys Pro Leu Glu Asp Phe Lys Ala Lys Val Val Thr Pro His Leu Lys
            435                 440                 445
His Ala Phe Asp Asn Leu Cys Asn Ala Asp Leu Asn Asp Leu Lys Gln
            450                 455                 460
Lys Pro Ala Ser Ser Lys Leu Ser Ile Leu Ser Ser Trp Leu Phe Gly
465                 470                 475                 480
Ser Ser His Asp Thr Glu Leu
                485

<210> SEQ ID NO 9
<211> LENGTH: 393
<212> TYPE: DNA
<213> ORGANISM: Arabidopsis thaliana

<400> SEQUENCE: 9
atggaggaag aagaaggatc aatccgacca gagtttccaa tcggaagagt aaagaagata      60
atgaaactgg acaagacat caacaaaatc aactcagaag ctcttcacgt catcacttac      120
tccaccgaac tcttcctcca cttcctcgcc gagaaatctg ctgttgttac ggcggagaag      180
aagcgtaaga ctgttaatct cgatcattta agaatcgccg tgaaaagaca ccaacctact      240
agtgatttcc tcttagactc gcttccgttg ccggctcagc ctgtcaaaca taccaaatcg      300
```

```
gtttccgaca agaagattcc ggcgccgcca attgggactc gtcgtatcga tgatttcttc    360
agtaaaggga aagcaaagac tgattcagcc taa                                 393

<210> SEQ ID NO 10
<211> LENGTH: 130
<212> TYPE: PRT
<213> ORGANISM: Arabidopsis thaliana

<400> SEQUENCE: 10

Met Glu Glu Glu Gly Ser Ile Arg Pro Glu Phe Pro Ile Gly Arg
1               5                   10                  15

Val Lys Lys Ile Met Lys Leu Asp Lys Asp Ile Asn Lys Ile Asn Ser
            20                  25                  30

Glu Ala Leu His Val Ile Thr Tyr Ser Thr Glu Leu Phe Leu His Phe
        35                  40                  45

Leu Ala Glu Lys Ser Ala Val Val Thr Ala Glu Lys Lys Arg Lys Thr
    50                  55                  60

Val Asn Leu Asp His Leu Arg Ile Ala Val Lys Arg His Gln Pro Thr
65                  70                  75                  80

Ser Asp Phe Leu Leu Asp Ser Leu Pro Leu Pro Ala Gln Pro Val Lys
                85                  90                  95

His Thr Lys Ser Val Ser Asp Lys Lys Ile Pro Ala Pro Pro Ile Gly
            100                 105                 110

Thr Arg Arg Ile Asp Asp Phe Phe Ser Lys Gly Lys Ala Lys Thr Asp
        115                 120                 125

Ser Ala
    130

<210> SEQ ID NO 11
<211> LENGTH: 3939
<212> TYPE: DNA
<213> ORGANISM: Arabidopsis thaliana

<400> SEQUENCE: 11
aaaagatacg ccttttttct tgttctgttt tgttttgcat gtcacagtaa gtaactctcc      60
tcctcaatta tcaaaaatgc aaactttaat tttcttctag agaagagcca ctctctccac    120
ttctttcttt gtccaacttt ttagacagag aaagtggcgt cagagataga tagagagata    180
catattcaag ttggttgaag gaggagaatt agcggttcat atcagtacgg agaaaattgt    240
cagtcatatg cttttttttct ttaaattctg catttgagtg ggtgtgtgct tttaaccatt    300
ttggtgattt atcaaaaaaa aaaaaaaaat tctgtgtgtt ttgagctcaa gctctctaca    360
aattttgctg tctcaagttt ttgccttttg aagtccaata aagttgaaat ctttgttctt    420
tttgattggt cttcgtgaat tccggtgaaa gtttcaaact tttgatttaa attccgggga    480
ggaattaggg tttatgaaag taaaagaaga actttgaag aatttgggag atggagtggt    540
tttaagacct gttgatcatt gttctagcat ttggagtatg aagatgaaca tgaagaactt    600
tcttaagaaa cttcatatct cgcccaatca atcagatgaa gctgaaggat caatttcaac    660
aactaagagc aatcatcata agtctatcga tgtatcatca tcatcatcac cgaggtctca    720
tcacagcaat agccctgaaa tcaaaccttt tctggtttta tctaattggt taagttctgt    780
tggtcataga aaaatcccta gtcctcctaa ttctttcaat gccaagaaca gagccgccac    840
ggttgatgac actgttgttg ttaatgggtc agaacatgtg gatttaggtt ccaaagatcc    900
agctgttgaa gaagagaatc agatacagtt ggctttagag ttaagtgcta gagaagatcc    960
```

```
tgaggctact cagattgagg ctattaagca attcagttta ggctcttgtg ctcctgagaa    1020
ctctccagct gaactcatcg cttatcgcta ctggaattac aattgtcttg gctatgatga    1080
caagatcttg gatggttttt atgacttgta tggagtgttg aatgcatcct cagcagaaag    1140
aatacctcct ttgctcgatc ttcaagggac acctgtttca gacggtgtga catgggaagc    1200
tgttcttgtg aacagaagtg gggattctaa tctgttgaga cttgaacaga tggctcttga    1260
tattgctgct aaatcaagat cagtttcttc ctctggtttt gtgaatagtg aattggtaag    1320
gaaactggct attttagtgg gagattacat gggtggacca gtcgtgcacc cagagagcat    1380
gttgagagct tggaggagtc ttagctatag tttgaaagca actcttggaa gcatggtttt    1440
gccacttggt tctctgacta ttggtttggc tcgtcaccga gccttgttat tcaaagtatt    1500
gtgtgatagt gttggtgttc cttgtcgaat agtcaaaggt cagcaatata ccggttctga    1560
agatgtggca atgaacttta ttaaggctga tgatggcagg gagtacattg ttgatcttat    1620
gggagatccc ggcacgctta ttccagctga tgcagctgga ctacaaatag actatgatga    1680
atctgcctat tccgctagtc ctggagacaa tgattcaatt catgtagctt cttccagcaa    1740
tggtattgaa agctcatatg aagagaatac agagtttcga acaggggaac atcgttctag    1800
taccaagagt tctggggaga gaaaccaatc cggaggtgga ggcgatctca ttgttcatcc    1860
aaatatttct agagaagatg tgaaaaatca gaagaaagtt gaaaaggctc catttcaaaa    1920
tctgtctagc aggcctattc attctttcac ccatatgaga tcaccttctt ggactgaagg    1980
ggttagctcc ccagctgcac aaaggatgaa agtcaaagat gtttcacaat atatgattga    2040
tgctgctaaa gagaatccac ggttagctca gaagcttcat gatgtattac ttgaaagcgg    2100
agttgtagct cctcccaatt tattttccga agtctatccc cagcaattgg aggcaactgt    2160
tgaaagcaaa aactcgactg aagccaagaa agagagagga aaagatttag agacaactca    2220
ggaaggaaga caccaaaaacg gttttggtcc agtgaggttt ttgcctccat taccaagagt    2280
gcaatctaaa acaaatgcac atgatcaacg tgataatggc aaagttgtaa gtcagtctga    2340
ttcttcacat tctgaagcat cttcgacaga atatgccaga accgtccctg ctgctgtagc    2400
tgcagctgct gttgttgcat cttccatggt tgctgctgct gctgccaagt ctgcaaactc    2460
agactcctcc cccatagaac ttcctgctgc agctgctgcc acggccactg ctgctgcagt    2520
tgtggcaaca gctgcagccg tgtccaggca acttgaatta ggctcgaata gcgacgggga    2580
tgatggttct ggtgggcatg agcctcaagg tagtggggac tctaatcatg gccaaattc    2640 aggagggaa agaatatctg acaaatctat tggcaatgaa agttctaagt cagactgtga    2700
tgatgtatct gactgtgaga ttttgtggga agaaattact gtgggagaac gtattggact    2760
tggatcttat ggagaagtgt atcggggaga ttggcacggg actgaagtgg ctgtcaagaa    2820
gttccttgat caagatttaa caggagaagc attggaggaa ttcagaagtg aggtccgaat    2880
catgaaaaag ctaagacatc ccaacattgt tctcttcatg ggagctgtga ctcgcccacc    2940
gaatctttca attgttacag agtttcttcc tagaggtagc ttgtataggt taatccaccg    3000
gccaaataac caattagacg agaggaggcg cctgagaatg gcccttgatg ctgctcgtgg    3060
aatgaactat ttgcacagct gtaatccgat gattgtccat cgcgatctta agtccccaaa    3120
ccttctagtt gacaaaaact gggtcgtgaa ggtgtgtgat tttggattgt ctaggatgaa    3180
acacagtaca tacctctctt caaagtcaac agcagggacg gctgaatgga tggctccaga    3240
agtgctaaga aacgaacctg ctgatgagaa gtgcgatgtt tacagctacg gtgtgatctt    3300
```

```
atgggaactc tttacgttac aacaaccgtg gggaaagatg aacccgatgc aagtagttgg    3360
gcagttgggt ttcagcatcg acgtcttgac attcccgact tgtagatcc agcaattgca    3420 gatctcatca gtaaatgctg gcagacggat tcaaagttaa ggccaagttt tgcagagata    3480
atggcgtctc taaagcggct acagaaacct gtaacaggtt ccaacatccc aagaccagtc    3540
cccagttcct cttcattacc aactgaacat gaacaaaagg attgataaca gaagaagacg    3600
accaaagtgg caaacacatt tttgacgaat tcaatctgtt tgaaggaaaa aaaagctaca    3660
aatgttcctt ctctgctact ttttgcctca gcttcagtgt ttgacacagc ttgtgaattg    3720
tgaaaaagaa agattcatgg aagatgacga ttgaagaagg tgaaggattg tgctcgtgtg    3780
ttttgttgtc tttgcttgca agcgatgttc atgttcatgc gtaatttcct ctattttgtt    3840
ttccaatatt gaaactgtac aaagagagaa agaaaaaaca attgacaaac tcgtcgaaac    3900
gttgaccgaa aacatatatt aaaaaaaatc attgagctc                          3939
```

<210> SEQ ID NO 12
<211> LENGTH: 1030
<212> TYPE: PRT
<213> ORGANISM: Arabidopsis thaliana

<400> SEQUENCE: 12

```
Met Lys Val Lys Glu Glu Thr Leu Lys Asn Leu Gly Asp Gly Val Val
1               5                   10                  15

Leu Arg Pro Val Asp His Cys Ser Ser Ile Trp Ser Met Lys Met Asn
            20                  25                  30

Met Lys Asn Phe Leu Lys Lys Leu His Ile Ser Pro Asn Gln Ser Asp
        35                  40                  45

Glu Ala Glu Gly Ser Ile Ser Thr Thr Lys Ser Asn His His Lys Ser
    50                  55                  60

Ile Asp Val Ser Ser Ser Ser Pro Arg Ser His His Ser Asn Ser
65                  70                  75                  80

Pro Glu Ile Lys Pro Phe Ser Gly Leu Ser Asn Trp Leu Ser Val
                85                  90                  95

Gly His Arg Lys Ile Pro Ser Pro Asn Ser Phe Asn Ala Lys Asn
            100                 105                 110

Arg Ala Ala Thr Val Asp Asp Thr Val Val Asn Gly Ser Glu His
        115                 120                 125

Val Asp Leu Gly Ser Lys Asp Pro Ala Val Glu Glu Asn Gln Ile
    130                 135                 140

Gln Leu Ala Leu Glu Leu Ser Ala Arg Glu Asp Pro Glu Ala Thr Gln
145                 150                 155                 160

Ile Glu Ala Ile Lys Gln Phe Ser Leu Gly Ser Cys Ala Pro Glu Asn
                165                 170                 175

Ser Pro Ala Glu Leu Ile Ala Tyr Arg Tyr Trp Asn Tyr Asn Cys Leu
            180                 185                 190

Gly Tyr Asp Asp Lys Ile Leu Asp Gly Phe Tyr Asp Leu Tyr Gly Val
        195                 200                 205

Leu Asn Ala Ser Ser Ala Glu Arg Ile Pro Pro Leu Leu Asp Leu Gln
    210                 215                 220

Gly Thr Pro Val Ser Asp Gly Val Thr Trp Glu Ala Val Leu Val Asn
225                 230                 235                 240

Arg Ser Gly Asp Ser Asn Leu Leu Arg Leu Glu Gln Met Ala Leu Asp
                245                 250                 255

Ile Ala Ala Lys Ser Arg Ser Val Ser Ser Ser Gly Phe Val Asn Ser
```

-continued

```
                260                 265                 270
Glu Leu Val Arg Lys Leu Ala Ile Leu Val Gly Asp Tyr Met Gly Gly
                275                 280                 285
Pro Val Val His Pro Glu Ser Met Leu Arg Ala Trp Arg Ser Leu Ser
            290                 295                 300
Tyr Ser Leu Lys Ala Thr Leu Gly Ser Met Val Leu Pro Leu Gly Ser
305                 310                 315                 320
Leu Thr Ile Gly Leu Ala Arg His Arg Ala Leu Leu Phe Lys Val Leu
                325                 330                 335
Cys Asp Ser Val Gly Val Pro Cys Arg Ile Val Lys Gly Gln Gln Tyr
            340                 345                 350
Thr Gly Ser Glu Asp Val Ala Met Asn Phe Ile Lys Ala Asp Asp Gly
            355                 360                 365
Arg Glu Tyr Ile Val Asp Leu Met Gly Asp Pro Gly Thr Leu Ile Pro
        370                 375                 380
Ala Asp Ala Ala Gly Leu Gln Ile Asp Tyr Asp Glu Ser Ala Tyr Ser
385                 390                 395                 400
Ala Ser Pro Gly Asp Asn Asp Ser Ile His Val Ala Ser Ser Ser Asn
                405                 410                 415
Gly Ile Glu Ser Ser Tyr Glu Glu Asn Thr Glu Phe Arg Thr Gly Glu
                420                 425                 430
His Arg Ser Ser Thr Lys Ser Ser Gly Glu Arg Asn Gln Ser Gly Gly
            435                 440                 445
Gly Gly Asp Leu Ile Val His Pro Asn Ile Ser Arg Glu Asp Val Lys
        450                 455                 460
Asn Gln Lys Lys Val Glu Lys Ala Pro Phe Gln Asn Leu Ser Ser Arg
465                 470                 475                 480
Pro Ile His Ser Phe Thr His Met Arg Ser Pro Ser Trp Thr Glu Gly
                485                 490                 495
Val Ser Ser Pro Ala Ala Gln Arg Met Lys Val Lys Asp Val Ser Gln
            500                 505                 510
Tyr Met Ile Asp Ala Ala Lys Glu Asn Pro Arg Leu Ala Gln Lys Leu
            515                 520                 525
His Asp Val Leu Leu Glu Ser Gly Val Val Ala Pro Pro Asn Leu Phe
        530                 535                 540
Ser Glu Val Tyr Pro Gln Gln Leu Glu Ala Thr Val Glu Ser Lys Asn
545                 550                 555                 560
Ser Thr Glu Ala Lys Lys Glu Arg Gly Lys Asp Leu Glu Thr Thr Gln
                565                 570                 575
Glu Gly Arg His Gln Asn Gly Phe Gly Pro Val Arg Phe Leu Pro Pro
            580                 585                 590
Leu Pro Arg Val Gln Ser Lys Thr Asn Ala His Asp Gln Arg Asp Asn
            595                 600                 605
Gly Lys Val Val Ser Gln Ser Asp Ser Ser His Ser Glu Ala Ser Ser
        610                 615                 620
Thr Glu Tyr Ala Arg Thr Val Pro Ala Val Ala Ala Ala Val
625                 630                 635                 640
Val Ala Ser Ser Met Val Ala Ala Ala Lys Ser Ala Asn Ser
                645                 650                 655
Asp Ser Ser Pro Ile Glu Leu Pro Ala Ala Ala Ala Thr Ala Thr
            660                 665                 670
Ala Ala Ala Val Val Ala Thr Ala Ala Val Ser Arg Gln Leu Glu
        675                 680                 685
```

Leu Gly Ser Asn Ser Asp Gly Asp Gly Ser Gly His Glu Pro
    690                 695                 700

Gln Gly Ser Gly Asp Ser Asn His Gly Pro Asn Ser Gly Gly Glu Arg
705                 710                 715                 720

Ile Ser Asp Lys Ser Ile Gly Asn Glu Ser Ser Lys Ser Asp Cys Asp
                725                 730                 735

Asp Val Ser Asp Cys Glu Ile Leu Trp Glu Ile Thr Val Gly Glu
                740                 745                 750

Arg Ile Gly Leu Gly Ser Tyr Gly Glu Val Tyr Arg Gly Asp Trp His
            755                 760                 765

Gly Thr Glu Val Ala Val Lys Lys Phe Leu Asp Gln Asp Leu Thr Gly
770                 775                 780

Glu Ala Leu Glu Glu Phe Arg Ser Glu Val Arg Ile Met Lys Lys Leu
785                 790                 795                 800

Arg His Pro Asn Ile Val Leu Phe Met Gly Ala Val Thr Arg Pro Pro
                805                 810                 815

Asn Leu Ser Ile Val Thr Glu Phe Leu Pro Arg Gly Ser Leu Tyr Arg
                820                 825                 830

Leu Ile His Arg Pro Asn Asn Gln Leu Asp Glu Arg Arg Leu Arg
            835                 840                 845

Met Ala Leu Asp Ala Ala Arg Gly Met Asn Tyr Leu His Ser Cys Asn
    850                 855                 860

Pro Met Ile Val His Arg Asp Leu Lys Ser Pro Asn Leu Leu Val Asp
865                 870                 875                 880

Lys Asn Trp Val Val Lys Val Cys Asp Phe Gly Leu Ser Arg Met Lys
                885                 890                 895

His Ser Thr Tyr Leu Ser Ser Lys Ser Thr Ala Gly Thr Ala Glu Trp
                900                 905                 910

Met Ala Pro Glu Val Leu Arg Asn Glu Pro Ala Asp Glu Lys Cys Asp
            915                 920                 925

Val Tyr Ser Tyr Gly Val Ile Leu Trp Glu Leu Phe Thr Leu Gln Gln
    930                 935                 940

Pro Trp Gly Lys Met Asn Pro Met Gln Val Val Gly Ala Val Gly Phe
945                 950                 955                 960

Gln His Arg Arg Leu Asp Ile Pro Asp Phe Val Asp Pro Ala Ile Ala
                965                 970                 975

Asp Leu Ile Ser Lys Cys Trp Gln Thr Asp Ser Lys Leu Arg Pro Ser
            980                 985                 990

Phe Ala Glu Ile Met Ala Ser Leu  Lys Arg Leu Gln Lys  Pro Val Thr
            995                  1000                1005

Gly Ser  Asn Ile Pro Arg Pro  Val Pro Ser Ser  Ser Leu Pro
    1010                1015                1020

Thr Glu  His Glu Gln Lys Asp
    1025                1030

<210> SEQ ID NO 13
<211> LENGTH: 1185
<212> TYPE: DNA
<213> ORGANISM: Arabidopsis thaliana

<400> SEQUENCE: 13
tcgattcaca aattattacg attgcaatcc ctaatttgga agtcccggtt cctctttcga    60
tcaaatcgga gaatttcacg gcatggctac ggctgttggt ggcggaagcg atgtggaggt   120

```
tggatttgcg aagcttcaag gtgaggattt cgagtactat atgcagtctt actccattat      180
actcggccgg aattctaaga aagccaccgt cgacgttgat ctctcatccc tcggcggtgg      240
gatgaacatc tcgcgcaacc acgctcggat cttctatgac ttcactagac gacgcttctc      300
tctcgaggtc cttggcaaaa atggctgcct cgttgaaggt gttcttcatc tccctgggaa      360
tcctaacgtc aagctcgatt cacaagacct tttgcagatc ggagacaaag agttctactt      420
tctcctaccg gttcggagca tcttaggcgg gccgttggga cctaggcacc acgtctctgg      480
gcaaacaagt gttgttccat accataatta tcagtcgggt ccaggttctg gtcgggtaa       540
gaagggcgtc aggagtagag agttgtatga gtacgatgat gaagatgatg atgacgacga      600
cgatgaggag gacgatatga gaggaagtgg aaagaaaaca aggagagatg gacatgaagt      660
agtatatgct tccggagaga agaagagaga gggaagatca aaggtagatc gtgaagctga      720
tgatcaacaa ttttttgcagc tggaggaaaa agatgttgta tcgtctgttg ccactgtgct      780
ttccgatttg tgtggtccgg gagagtggat gcctatggaa aaacttcatt cggtgatatt      840
aaaggagtat ggaaacgtat ggcatcacag tcgagtaaga agatacctat cacaagaaga      900
ctgggctatc cctgaagcaa aaggtaaacc atggtacggt ttgctgatgc tgctgagaaa      960
ataccccggag catttcgtca tcaacacgag atcaagggga gagttaccc ttgaattcgt     1020
ttccctcgtt accctactct catgagaact ttaccttagt gactcggatt aagatttaag     1080
aagcttttct ctctttttctt tgtttcatat gtaaatatt ttggcattga ttagtaacac     1140
gctgtgtcgt ttttctgcac ccaaaaacgc caacttcttg gtcct                     1185
```

<210> SEQ ID NO 14
<211> LENGTH: 320
<212> TYPE: PRT
<213> ORGANISM: Arabidopsis thaliana

<400> SEQUENCE: 14

Met Ala Thr Ala Val Gly Gly Ser Asp Val Glu Val Gly Phe Ala
1               5                   10                  15

Lys Leu Gln Gly Glu Asp Phe Glu Tyr Tyr Met Gln Ser Tyr Ser Ile
            20                  25                  30

Ile Leu Gly Arg Asn Ser Lys Lys Ala Thr Val Asp Val Asp Leu Ser
        35                  40                  45

Ser Leu Gly Gly Gly Met Asn Ile Ser Arg Asn His Ala Arg Ile Phe
    50                  55                  60

Tyr Asp Phe Thr Arg Arg Arg Phe Ser Leu Glu Val Leu Gly Lys Asn
65                  70                  75                  80

Gly Cys Leu Val Glu Gly Val Leu His Leu Pro Gly Asn Pro Asn Val
                85                  90                  95

Lys Leu Asp Ser Gln Asp Leu Leu Gln Ile Gly Asp Lys Glu Phe Tyr
            100                 105                 110

Phe Leu Leu Pro Val Arg Ser Ile Leu Gly Gly Pro Leu Gly Pro Arg
        115                 120                 125

His His Val Ser Gly Gln Thr Ser Val Val Pro Tyr His Asn Tyr Gln
    130                 135                 140

Ser Gly Pro Gly Ser Gly Ser Gly Lys Lys Gly Val Arg Ser Arg Glu
145                 150                 155                 160

Leu Tyr Glu Tyr Asp Asp Glu Asp Asp Asp Asp Asp Asp Glu Glu
            165                 170                 175

Asp Asp Met Arg Gly Ser Gly Lys Lys Thr Arg Arg Asp Gly His Glu
        180                 185                 190

-continued

```
Val Val Tyr Ala Ser Gly Glu Lys Lys Arg Glu Gly Arg Ser Lys Val
        195                 200                 205

Asp Arg Glu Ala Asp Asp Gln Gln Phe Leu Gln Leu Glu Glu Lys Asp
        210                 215                 220

Val Val Ser Ser Val Ala Thr Val Leu Ser Asp Leu Cys Gly Pro Gly
225                 230                 235                 240

Glu Trp Met Pro Met Glu Lys Leu His Ser Val Ile Leu Lys Glu Tyr
                245                 250                 255

Gly Asn Val Trp His His Ser Arg Val Arg Arg Tyr Leu Ser Gln Glu
            260                 265                 270

Asp Trp Ala Ile Pro Glu Ala Lys Gly Lys Pro Trp Tyr Gly Leu Leu
        275                 280                 285

Met Leu Leu Arg Lys Tyr Pro Glu His Phe Val Ile Asn Thr Arg Ser
        290                 295                 300

Lys Gly Arg Val Thr Leu Glu Phe Val Ser Leu Val Thr Leu Leu Ser
305                 310                 315                 320
```

GENERATION OF PLANTS WITH ALTERED OIL, PROTEIN, OR FIBER CONTENT

CROSS REFERENCE TO RELATED APPLICATION(S)

This is a divisional of U.S. patent application Ser. No. 11/956,228, filed on Dec. 13, 2007, and now U.S. Pat. No. 7,563,943 which claims the benefit of U.S. Provisional Application No. 60/870,355, filed Dec. 15, 2006, both of which are incorporated herein by reference in their entirety.

FIELD OF THE DISCLOSURE

The present disclosure is related to modified plants with altered oil, protein, and/or fiber content, as well as methods of making modified plants having altered oil, protein, and/or fiber content and producing oil from such plants.

BACKGROUND

The ability to manipulate the composition of crop seeds, particularly the content and composition of seed oil and protein, as well as the available metabolizable energy ("AME") in the seed meal in livestock, has important applications in the agricultural industries, relating both to processed food oils and to animal feeds. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remaining seed meal is sold for livestock feed (U.S. Soybean Board, 2001 Soy Stats). Canola seed is also crushed to produce oil and the co-product canola meal (Canola Council of Canada). Canola meal contains a high percentage of protein and a good balance of amino acids but because it has a high fiber and phytate content, it is not readily digested by livestock (Slominski, B. A., et al., 1999 Proceedings of the 10$^{th}$ International Rapeseed Congress, Canberra, Australia) and has a lower value than soybean meal.

Over 55% of the corn produced in the U.S. is used as animal feed (Iowa Corn Growers Association). The value of the corn is directly related to its ability to be digested by livestock. Thus, it is desirable to maximize both oil content of seeds and the AME of meal. For processed oilseeds such as soy and canola, increasing the absolute oil content of the seed will increase the value of such grains, while increasing the AME of meal will increase its value. For processed corn, either an increase or a decrease in oil content may be desired, depending on how the other major constituents are to be used. Decreasing oil may improve the quality of isolated starch by reducing undesired flavors associated with oil oxidation. Alternatively, when the starch is used for ethanol production, where flavor is unimportant, increasing oil content may increase overall value.

In many feed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors. In addition, increasing the AME of meal by adjusting seed protein and fiber content and composition, without decreasing seed oil content, can increase the value of animal feed.

Biotechnological manipulation of oils has been shown to provide compositional alteration and improvement of oil yield. Compositional alterations include high oleic acid soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds, but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil content in current HOC fields has not been able to achieve seed oil content above 9%. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

Manipulation of seed composition has identified several components that improve the nutritive quality, digestibility, and AME in seed meal. Increasing the lysine content in canola and soybean (Falco et al., 1995 *Bio/Technology* 13:577-582) increases the availability of this essential amino acid and decreases the need for nutritional supplements. Soybean varieties with increased seed protein were shown to contain considerably more metabolizable energy than conventional varieties (Edwards et al., 1999, *Poultry Sci.* 79:525-527). Decreasing the phytate content of corn seed has been shown to increase the bioavailability of amino acids in animal feeds (Douglas et al., 2000, *Poultry Sci.* 79:1586-1591) and decreasing oligosaccharide content in soybean meal increases the metabolizable energy in the meal (Parsons et al., 2000, *Poultry Sci.* 79:1127-1131).

Soybean and canola are the most obvious target crops for the processed oil and seed meal markets since both crops are crushed for oil and the remaining meal sold for animal feed. A large body of commercial work (e.g., U.S. Pat. No. 5,952,544; PCT Application No. WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990, *Theor. Appl. Genet.* 80: 234-240; James and Dooner, 1990, *Theor. Appl. Genet.* 80: 241-245). T-DNA mutagenesis screens (Feldmann et al., 1989, *Science* 243: 1351-1354) that detected altered fatty acid composition identified the omega 3 desaturase (FAD3) and delta-12 desaturase (FAD2) genes (U.S. Pat. No 5,952,544; Yadav et al., 1993, *Plant Physiol.* 103: 467-476; Okuley et al., 1994, *Plant Cell* 6(1):147-158). A screen which focused on oil content rather than oil quality, analyzed chemically-induced mutants for wrinkled seeds or altered seed density, from which altered seed oil content was inferred (Focks and Benning, 1998, *Plant Physiol.* 118:91-101).

Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al., 1995, *Plant Physiol.* 108(1):399-409). It was further shown that seed-specific over-expression of the DGAT cDNA was associated with increased seed oil content (Jako et al., 2001, *Plant Physiol.* 126(2):861-74). *Arabidopsis* is also a model for understanding the accumulation of seed components that affect meal quality. For example, *Arabidopsis* contains albumin and globulin seed storage proteins found in many dicotyledonous plants including canola and soybean (Shewry 1995, *Plant Cell* 7:945-956). The biochemical pathways for synthesizing components of fiber, such as cellulose and lignin, are conserved within the vascular plants, and mutants of *Arabidopsis* affecting these components have been isolated (reviewed in Chapel and Carpita 1998, *Current Opinion in Plant Biology* 1:179-185).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992, *Science* 258: 1350-1353; Weigel D et al., 2000, *Plant Physiology*, 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, *Plant Cell* 8: 659-671; Schaffer et al., 1998, *Cell* 93: 1219-1229; Fridborg et al., 1999, *Plant Cell* 11: 1019-1032; Kardailsky et al., 1999, *Science* 286: 1962-1965; and Christensen S et al., 1998, *9th International Conference on Arabidopsis Research*, Univ. of Wisconsin-Madison, June 24-28, Abstract 165).

SUMMARY

Provided herein are modified plants having an altered phenotype. Modified plants with an altered phenotype may include an improved oil quantity and/or an improved meal quality phenotype. The altered phenotype in a modified plant may also include altered oil, protein, and/or fiber content in any part of the modified plant, for example in the seeds. In some embodiments of a modified plant, the altered phenotype is an increase in the oil content of the seed (a high oil phenotype). In other embodiments, the altered phenotype may be an increase in protein content in the seed and/or a decrease in the fiber content of the seed. Also provided is seed meal derived from the seeds of modified plants, wherein the seeds have altered protein content and/or altered fiber content. Further provided is oil derived from the seeds of modified plants, wherein the seeds have altered oil content. Any of these changes can lead to an increase in the AME from the seed or seed meal from modified plants, relative to control or wild-type plants. Also provided herein is meal, feed, or food produced from any part of the modified plant with an altered phenotype.

In certain embodiments, the disclosed modified plants include transgenic plants having a transformation vector comprising a HIO nucleotide sequence (or HIO gene alias) that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Examples of the disclosed transgenic plant are produced by a method that comprises introducing into progenitor cells of the plant a plant transformation vector comprising a HIO nucleotide sequence that encodes, or is complementary to a sequence that encodes, a HIO polypeptide, and growing the transformed progenitor cells to produce a transgenic plant, wherein the HIO polynucleotide sequence is expressed, causing an altered phenotype in the transgenic plant. In some specific, non-limiting examples, the method produces transgenic plants wherein expression of the HIO polypeptide causes a high (increased) oil, high (increased) protein, and/or low (decreased) fiber phenotype in the transgenic plant, relative to control, non-transgenic, or wild-type plants.

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen, radiation, or ultraviolet light. In some embodiments of the method, the plant is bred to generate progeny which inherit the allele and express the altered phenotype. In particular embodiments of the method, the method employs candidate gene/QTL methodology or TILLING methodology.

Also provided herein is a modified plant cell having an altered phenotype. In some embodiments, the modified plant cell includes a transformation vector comprising a HIO nucleotide sequence that encodes or is complementary to a sequence that encodes a HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells.

DETAILED DESCRIPTION

Terms

Unless otherwise indicated, all technical and scientific terms used herein have the same meaning as they would to one skilled in the art of the present disclosure. Practitioners are particularly directed to Sambrook et al. (*Molecular Cloning: A Laboratory Manual* (Second Edition), Cold Spring Harbor Press, Plainview, N.Y., 1989) and Ausubel F M et al. (*Current Protocols in Molecular Biology*, John Wiley & Sons, New York, N.Y., 1993) for definitions and terms of the art. It is to be understood that this disclosure is not limited to the particular methodology, protocols, and reagents described, as these may vary.

As used herein, the term "altered phenotype" refers to plants, or any part of a plant (for example, seeds, or meal produced from seeds), with an altered oil, protein, and/or fiber content (phenotype). As provided herein, altered oil, protein (for example, digestible protein) and/or fiber content includes either an increased or decreased level of oil, protein (for example, digestible protein) and/or fiber content in plants, seeds or seed meal. Any combination of these changes can lead to an altered phenotype. For example, in one specific non-limiting example, an altered phenotype can refer to increased oil and decreased fiber content. In another specific non-limiting example, an altered phenotype can refer to unchanged protein and decreased fiber content. In another specific non-limiting example, an altered phenotype can refer to increased oil and protein and decreased fiber. In yet other non-limiting examples, an altered phenotype can refer to increased oil and protein and unchanged fiber content; unchanged oil, increased protein, and decreased fiber content; or increased oil, increased protein, and decreased fiber content. It is also provided that any combination of these changes can lead to an increase in the AME (available metabolizable energy) from the seed or meal generated from the seed. An altered phenotype also includes an improved seed quality (ISQ) phenotype or an improved seed meal quality phenotype.

As used herein, the term "available metabolizable energy" (AME) refers to the amount of energy in the feed that is able to be extracted by digestion in an animal and is correlated with the amount of digestible protein and oil available in animal meal. AME is determined by estimating the amount of energy in the feed prior to feeding and measuring the amount of energy in the excreta of the animal following consumption of the feed. In one specific, non-limiting example, a modified plant with an increase in AME includes modified plants with altered seed oil, digestible protein, total protein and/or fiber content, resulting in an increase in the value of animal feed derived from the seed.

As used herein, the term "content" refers to the type and relative amount of, for instance, a seed or seed meal component.

As used herein, the term "seed oil" refers to the total amount of oil within the seed.

As used herein, the term "seed fiber" refers to non-digestible components of the plant seed including cellular components such as cellulose, hemicellulose, pectin, lignin, and phenolics.

As used herein, the term "meal" refers to seed components remaining following the extraction of oil from the seed. Examples of components of meal include protein and fiber.

As used herein, the term "seed total protein" refers to the total amount of protein within the seed.

As used herein, the term "seed digestible protein" refers to the seed protein that is able to be digested by enzymes in the digestive track of an animal. It is a subset of the total protein content.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell by infection, transfection, microinjection, electroporation, or the like. A "heterologous" nucleic acid construct may contain a control sequence/DNA coding sequence combination that is the same as, or different from, a control sequence/DNA coding sequence combination found in the native plant. Specific, non-limiting examples of a heterologous nucleic acid sequence include a HIO nucleic acid sequence, or a fragment, derivative (variant), or ortholog or paralog thereof.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequences.

The term "homolog" refers to any gene that is related to a reference gene by descent from a common ancestral DNA sequence. The term "ortholog" refers to homologs in different species that evolved from a common ancestral gene by speciation. Typically, orthologs retain the same or similar function despite differences in their primary structure (mutations). The term "paralog" refers to homologs in the same species that evolved by genetic duplication of a common ancestral gene. In many cases, paralogs exhibit related (but not always identical functions). As used herein, the term homolog encompasses both orthologs and paralogs. To the extent that a particular species has evolved multiple related genes from an ancestral DNA sequence shared with another species, the term ortholog can encompass the term paralog.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed, or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-modified or wild-type plant. "Under-expression" refers to decreased expression of a polynucleotide and/or polypeptide sequence, generally of an endogenous gene, relative to its expression in a wild-type plant. The terms "mis-expression"

and "altered expression" encompass over-expression, under-expression, and ectopic expression.

The term "introduced" in the context of inserting a nucleic acid sequence into a cell, includes "transfection," "transformation," and "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus), as well as from plant seeds, pollen, propagules, and embryos.

As used herein, the terms "native" and "wild-type" relative to a given plant trait or phenotype refers to the form in which that trait or phenotype is found in the same variety of plant in nature. In one embodiment, a wild-type or native plant is also a control plant. In another embodiment, a wild-type or native plant is a non-transgenic or non-mutated plant. In yet another embodiment, a wild-type or native plant is a non-modified plant.

As used herein, the term "modified" regarding a plant, refers to a plant with an altered phenotype (for example, a plant generated by genetic engineering, mutagenesis, or breeding methods). A genetically engineered plant can also be a transgenic plant. In particular embodiments, modified plants generated by breeding methods are first mutagenized using any one of a variety of mutagens, such as a chemical mutagen, radiation, or ultraviolet light. Modified plants can have any combination of an altered oil content, an altered protein content, and/or an altered fiber content in any part of the transgenic plant, for example the seeds, relative to a similar non-modified plant.

As used herein, the term "altered" refers to a change (either an increase or a decrease) of a plant trait or phenotype (for example, oil content, protein content, and/or fiber content) in a modified plant, relative to a similar non-modified plant. In one specific, non-limiting example, a modified plant with an altered trait includes a plant with an increased oil content, increased protein content, and/or decreased fiber content relative to a similar non-modified plant. In another specific, non-limiting example, a modified plant with an altered trait includes unchanged oil content, increased protein content, and/or decreased fiber content relative to a similar non-modified plant. In yet another specific, non-limiting example, a modified plant with an altered trait includes an increased oil content, increased protein content, and/or unchanged fiber content relative to a similar non-modified plant.

An "interesting phenotype (trait)" with reference to a modified plant refers to an observable or measurable phenotype demonstrated by a T1 and/or subsequent generation plant, which is not displayed by the corresponding non-modified plant (i.e., a genotypically similar plant that has been raised or assayed under similar conditions). An interesting phenotype may represent an improvement in the plant (for example, increased oil content, increased protein content, and/or decreased fiber content in seeds of the plant) or may provide a means to produce improvements in other plants. An "improvement" is a feature that may enhance the utility of a plant species or variety by providing the plant with a unique and/or novel phenotype or quality. Such modified plants may have an improved phenotype, such as an altered oil, protein, and/or fiber phenotype. Meal generated from seeds of a modified plant with an improved phenotype can have improved (increased) meal quality. In a specific, non-limiting example of meal with an improved (increased) quality phenotype, meal is generated from a seed of a modified plant, wherein the seed has increased protein content and/or decreased fiber content, relative to a similar non-modified plant.

The phrase "altered oil content phenotype" refers to a measurable phenotype of a modified plant, where the plant displays a statistically significant increase or decrease in overall oil content (i.e., the percentage of seed mass that is oil), as compared to the similar, but non-modified (for example, a non-transgenic or a non-mutated) plant. A high oil phenotype refers to an increase in overall oil content. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. Likewise, a decrease in oil content includes about a 1.0%, 1.5%, 2.0%, 2.5%, 3.0%, 3.5%, 4.0%, 4.5%, 5.0%, 7.5%, 10%, or more decrease in oil content, in various embodiments.

The phrase "altered protein content phenotype" refers to measurable phenotype of a modified plant, where the plant displays a statistically significant increase or decrease in overall protein content (i.e., the percentage of seed mass that is protein), as compared to the similar, but non-modified (for example, non-transgenic or non-mutated) plant. A high protein phenotype refers to an increase in overall protein content. An increase in protein content includes, in various embodiments, about a 1.0%, 1.5%, 2.0%, 2.5%, 3.0%, 3.5%, 4.0%, 4.5%, 5.0%, 7.5%, 10%, or more increase in total protein content. Likewise, an increase in digestible protein content includes, in various embodiments, about a 1.0%, 1.5%, 2.0%, 2.5%, 3.0%, 3.5%, 4.0%, 4.5%, 5.0%, 7.5%, 10%, or more increase in digestible protein content. A decrease in protein content includes about a 1.0%, 1.5%, 2.0%, 2.5%, 3.0%, 3.5%, 4.0%, 4.5%, 5.0%, 7.5%, 10%, or more decrease in total protein content, in various embodiments. Likewise, a decrease in digestible protein content includes, in various embodiments, about a 1.0%, 1.5%, 2.0%, 2.5%, 3.0%, 3.5%, 4.0%, 4.5%, 5.0%, 7.5%, 10%, or more decrease in digestible protein content. The phrase "altered fiber content phenotype" refers to measurable phenotype of a modified plant, where the plant displays a statistically significant increase or decrease in overall fiber content (i.e., the percentage of seed mass that is fiber), as compared to the similar, but non-modified (for example, non-transgenic or non-mutated) plant. A low fiber phenotype refers to decrease in overall fiber content. An increase in fiber content includes about a 1.0%, 1.5%, 2.0%, 2.5%, 3.0%, 3.5%, 4.0%, 4.5%, 5.0%, 7.5%, 10%, or more increase in fiber content. Likewise, a decrease in fiber content includes about a 1.0%, 1.5%, 2.0%, 2.5%, 3.0%, 3.5%, 4.0%, 4.5%, 5.0%, 7.5%, 10%, or more decrease in fiber content.

As used herein, a "mutant" or "mutated" polynucleotide sequence or gene differs from the corresponding wild-type polynucleotide sequence or gene either in terms of sequence or expression, where the difference contributes to an altered plant phenotype or trait. Relative to a plant or plant line, the term "mutant" or "mutated" refers to a plant or plant line which has an altered plant phenotype or trait, where the altered phenotype or trait is associated with the altered expression of a wild-type polynucleotide sequence or gene. The mutated polynucleotide sequence or gene can be generated by genetic engineering methods (such as activation tagging or transformation), by using one or more mutagens (for example, chemical mutagens, radiation, or ultraviolet light), or by using methods to alter a DNA sequence (for example, error prone PCR, DNA shuffling molecular breeding, site-directed mutagenesis, or introducing the gene into a mutagenizing organism such as *E. coli* or yeast strains that are deficient in DNA repair activity).

As used herein, the term "T1" refers to the generation of plants from the seed of T0 plants. The T1 generation is the first set of modified plants that can be selected by application of a selection agent, e.g., an antibiotic or herbicide, for which the modified plant contains the corresponding resistance gene. The term "T2" refers to the generation of plants by self-fertilization of the flowers of T1 plants, previously selected as being modified. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. Provided herein is a modified plant cell having an altered phenotype. In particular embodiments, the modified plant cell is a transgenic plant cell. The transgenic plant cell includes a transformation vector comprising an HIO nucleotide sequence that encodes or is complementary to a sequence that encodes an HIO polypeptide. In preferred embodiments, the transgenic plant cell is selected from the group consisting of plants of the *Brassica* species, including canola and rapeseed, soy, corn, sunflower, cotton, cocoa, safflower, oil palm, coconut palm, flax, castor, peanut, wheat, oat and rice. In other embodiments, the plant cell is a seed, pollen, propagule, or embryo cell. The disclosure also provides plant cells from a plant that is the direct progeny or the indirect progeny of a plant grown from said progenitor cells. The class of plants which can be used in the methods of the present invention is generally as broad as the class of higher plants amenable to transformation techniques, including both monocotyledonous and dicotyledonous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed," "transfected," or "transgenic." Direct and indirect progeny of transformed plants or plant cells that also contain the heterologous polynucleotide are also considered transgenic.

Disclosed herein are modified plants having an altered phenotype. Modified plants with an altered phenotype may include an improved (increased) oil quantity and/or an improved (increased) meal quality, as compared to the similar, but non-modified (for example, non-transgenic or non-mutated) plant. Modified plants with an altered phenotype may include altered oil, protein, and/or fiber content in any part of the modified plant, for example in the seeds, as compared to the similar, but non-modified (for example, non-transgenic or non-mutated) plant. In some embodiments of a modified plant, for example in plants with an improved or increased oil content phenotype, the altered phenotype includes an increase in the oil content of the seed (a high oil phenotype) from the plant, as compared to the similar, but non-modified (non-transgenic or non-mutated) plant. An increase in oil content includes, in various embodiments, about a 1.0%, 1.5%, 2.0%, 2.5%, 3.0%, 3.5%, 4.0%, 4.5%, 5.0%, 7.5%, 10%, or more increase in oil content. The altered phenotype can be an increase in one or more fatty acids, such as oleic acid, with a concomitant decrease in other fatty acids such as linoleic or linolinic acids. A change in fatty acid content includes about a 5%, 10%, 20%, 30%, 40%, 50%, 60%, 70%, 80%, 90%, 100% or more increase in a specific fatty acid. In other embodiments of a modified plant, for example in plants with an improved or increased meal quality phenotype, the altered phenotype may be an increase in protein content in the seed and/or a decrease in the fiber content of the seed. An increase in protein content includes about a 1.0%, 1.5%, 2.0%, 2.5%, 3.0%, 3.5%, 4.0%, 4.5%, 5.0%, 7.5%, 10%, or more increase in protein content, for instance total protein content or digestible protein content. This change in seed protein content can be the result of altered amounts of seed storage proteins such as albumins, globulins prolamins, and glutelins. A decrease in fiber content includes about a 1.0%, 1.5%, 2.0%, 2.5%, 3.0%, 3.5%, 4.0%, 4.5%, 5.0%, 7.5%, 10%, or more decrease in fiber content. This change in fiber content can be the result of altered amounts of fibrous components such as cellulose, hemicellulose, lignin and pectins.

Also provided is seed meal derived from the seeds of modified plants, wherein the seeds have altered (for example, increased) protein (for example, digestible) content and/or altered (for example, decreased) fiber content. Further provided is oil derived from the seeds of modified plants, wherein the seeds have altered oil content. Any of these changes can lead to an increase in the AME from the seed or seed meal from modified plants, relative to control, non-transgenic, or wild-type plants. An increase in the AME includes about a 1.0%, 1.5%, 2.0%, 2.5%, 3.0%, 3.5%, 4.0%, 4.5%, 5.0%, 7.5%, 10%, or more increase in AME in the seed or seed meal, in various embodiments. Also provided herein is meal, feed, or food produced from any part of the modified plant with an altered phenotype.

In certain embodiments, the disclosed transgenic plants comprise a transformation vector comprising a HIO nucleotide sequence that encodes or is complementary to a sequence that encodes a "HIO" polypeptide. In particular embodiments, expression of a HIO polypeptide in a transgenic plant causes an altered oil content, an altered protein content, and/or an altered fiber content in the transgenic plant. In preferred embodiments, the transgenic plant is selected from the group consisting of plants of the *Brassica* species, including canola and rapeseed, soy, corn, sunflower, cotton, cocoa, safflower, oil palm, coconut palm, flax, castor, peanut, wheat, oat and rice. Also provided is a method of producing oil or seed meal, comprising growing the transgenic plant and recovering oil and/or seed meal from said plant. The disclosure further provides feed, meal, grain, or seed comprising a nucleic acid sequence that encodes a HIO polypeptide. The disclosure also provides feed, meal, grain, or seed comprising the HIO polypeptide, or an ortholog or paralog thereof.

Various methods for the introduction of a desired polynucleotide sequence encoding the desired protein into plant cells are available and known to those of skill in the art and include, but are not limited to: (1) physical methods such as microinjection, electroporation, and microprojectile mediated delivery (biolistics or gene gun technology); (2) virus mediated delivery methods; and (3) *Agrobacterium*-mediated transformation methods.

The most commonly used methods for transformation of plant cells are the *Agrobacterium*-mediated DNA transfer process and the biolistics or microprojectile bombardment mediated process (i.e., the gene gun). Typically, nuclear transformation is desired but where it is desirable to specifically transform plastids, such as chloroplasts or amyloplasts, plant plastids may be transformed utilizing a microprojectile-mediated delivery of the desired polynucleotide.

Agrobacterium-mediated transformation is achieved through the use of a genetically engineered soil bacterium belonging to the genus Agrobacterium. A number of wild-type and disarmed strains of Agrobacterium tumefaciens and Agrobacterium rhizogenes harboring Ti or Ri plasmids can be used for gene transfer into plants. Gene transfer is done via the transfer of a specific DNA known as "T-DNA" that can be genetically engineered to carry any desired piece of DNA into many plant species.

Agrobacterium-mediated genetic transformation of plants involves several steps. The first step, in which the virulent Agrobacterium and plant cells are first brought into contact with each other, is generally called "inoculation." Following the inoculation, the Agrobacterium and plant cells/tissues are permitted to be grown together for a period of several hours to several days or more under conditions suitable for growth and T-DNA transfer. This step is termed "co-culture." Following co-culture and T-DNA delivery, the plant cells are treated with bactericidal or bacteriostatic agents to kill or limit the growth of the Agrobacterium remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microprojectile bombardment (U.S. Pat. No. 5,550,318; U.S. Pat. No. 5,538,880, U.S. Pat. No. 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics Particle Delivery System (BioRad, Hercules, Calif.), which can be used to propel particles coated with DNA or cells through a screen, such as a stainless steel or Nytex screen, onto a filter surface covered with monocot plant cells cultured in suspension.

Microprojectile bombardment techniques are widely applicable, and may be used to transform virtually any plant species. Examples of species that have been transformed by microprojectile bombardment include monocot species such as maize (PCT Publication No. WO 95/06128), barley, wheat (U.S. Pat. No. 5,563,055, incorporated herein by reference in its entirety), rice, oat, rye, sugarcane, and sorghum, as well as a number of dicots including tobacco, soybean (U.S. Pat. No. 5,322,783, incorporated herein by reference in its entirety), sunflower, peanut, cotton, tomato, and legumes in general (U.S. Pat. No. 5,563,055, incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker would include but are not limited to GUS, green fluorescent protein (GFP), luciferase (LUX), antibiotic or herbicide tolerance genes. Examples of antibiotic resistance genes include the penicillins, kanamycin, neomycin, G418, bleomycin, methotrexate (and trimethoprim), chloramphenicol, and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061, U.S. Pat. No. 5,633,435, and U.S. Pat. No. 6,040,497 and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., (Plant J. 4:833-840, 1993) and Misawa et al., (Plant J. 6:481-489, 1994) for norflurazon tolerance; a polynucleotide molecule encoding acetohydroxyacid synthase (AHAS, also known as ALS) described in Sathasiivan et al. (Nucl. Acids Res. 18:2188-2193, 1990) for tolerance to sulfonylurea herbicides; and the bar gene described in DeBlock, et al., (EMBO J. 6:2513-2519, 1987) for glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

One of ordinary skill will appreciate that, after an expression cassette is stably incorporated in transgenic plants and confirmed to be operable, it can be introduced into other plants by sexual crossing. Any of a number of standard breeding techniques can be used, depending upon the species to be crossed.

Identification of Plants with an Altered Phenotype

An *Arabidopsis* activation tagging screen (ACTTAG) was used to identify the association between 1) ACTTAG plant lines with an altered oil, protein and/or fiber content (see columns 4, 5 and 6 respectively, of Table 1, below) and 2) the nucleic acid sequences identified in column 3 of Tables 2 and 3, wherein each nucleic acid sequence is provided with a gene alias or a HIO designation (HIO#; see column 1 in Tables 1, 2, and 3). The HIO designation is arbitrary and does not necessarily relate to a plant having a high oil (HIO) phenotype.

Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al., 2000, *Plant Physiology*, 122:1003-1013). When the T-DNA inserts into the genome of transformed plants, the enhancer element can cause up-regulation of genes in the vicinity, generally within about nine kilobases (kb) of the enhancers. T1 plants were exposed to the selective agent in order to specifically recover transformed plants that expressed the selectable marker and therefore harbored T-DNA insertions. T1 plants were allowed to grow to maturity, self-fertilize and produce seed. T2 seed was harvested, labeled and stored. To amplify the seed stocks, about eighteen T2 were sown in soil and, after germination, exposed to the selective agent to recover transformed T2 plants. T3 seed from these plants was harvested and pooled. Oil, protein and fiber content of the seed were estimated using Near Infrared Spectroscopy (NIR) as described in the Examples.

The association of a HIO nucleic acid sequence with an altered phenotype was discovered by analysis of the genomic DNA sequence flanking the T-DNA insertion in the ACTTAG line identified in column 3 of Table 1. An ACTTAG line is a family of plants derived from a single plant that was transformed with a T-DNA element containing four tandem copies of the CaMV 35S enhancers. Accordingly, the disclosed HIO nucleic acid sequences and/or polypeptides may be employed in the development of transgenic plants having an altered, for example high oil, phenotype. HIO nucleic acid sequences may be used in the generation of transgenic plants, such as oilseed crops, that provide improved oil yield from oilseed processing and result in an increase in the quantity of oil recovered from seeds of the transgenic plant. HIO nucleic acid sequences may also be used in the generation of transgenic plants, such as feed grain crops, that provide an altered phenotype resulting in increased energy for animal feeding, for example, seeds or seed meal with an altered protein and/or fiber content, resulting in an increase in AME. HIO nucleic acid sequences may further be used to increase the oil content of specialty oil crops, in order to augment yield and/or recovery of desired unusual fatty acids. Specific non-limiting examples of unusual fatty acids are ricinoleic acid, vernolic acid and the very long chain polyunsaturated fatty acids docosahexaenoic acid (DHA) and eicosapentaenoic acid (EPA). Transgenic plants that have been genetically modified to express HIO polypeptides can be used in the production of seeds, wherein the transgenic plants are grown, and oil and seed meal are obtained from plant parts (e.g. seed) using standard methods.

HIO Nucleic Acids and Polypeptides

The HIO designation for each of the HIO nucleic acid sequences discovered in the activation tagging screen described herein are listed in column 1 of Tables 1-3, below. The disclosed HIO polypeptides are listed in column 4 of Tables 2 and 3, below. The HIO designation is arbitrary and does not necessarily relate to a plant having a high oil (HIO) phenotype. As used herein, the gene alias or HIO designation refers to any polypeptide sequence (or the nucleic acid sequence that encodes it) that when expressed in a plant causes an altered phenotype in any part of the plant, for example the seeds. In one embodiment, a HIO polypeptide refers to a full-length HIO protein, or a fragment, derivative (variant), or ortholog or paralog thereof that is "functionally active," such that the protein fragment, derivative, or ortholog or paralog exhibits one or more or the functional activities associated with one or more of the disclosed full-length HIO polypeptides, for example, the amino acid sequences provided in the GenBank entry referenced in column 4 of Table 2, and 3 which correspond to the amino acid sequences set forth as SEQ ID NO: 2, SEQ ID NO: 4, SEQ ID NO: 6, SEQ ID NO: 8, SEQ ID NO: 10, SEQ ID NO: 12, or SEQ ID NO: 14, or an ortholog or paralog thereof. In one preferred embodiment, a functionally active HIO polypeptide causes an altered phenotype in a transgenic plant. In another embodiment, a functionally active HIO polypeptide causes an altered oil, protein, and/or fiber content phenotype (for example, an altered seed meal content phenotype) when mis-expressed in a plant. In other preferred embodiments, mis-expression of the HIO polypeptide causes a high oil (such as, increased oil), high protein (such as, increased total protein or digestible protein), and/or low fiber (such as, decreased fiber) phenotype in a plant. In yet other preferred embodiments, mis-expression of the HIO polypeptide causes unchanged oil, high protein (such as, increased total protein or digestible protein), and/or low fiber (such as, decreased fiber) phenotype in a plant. In another embodiment, mis-expression of the HIO polypeptide causes an improved AME of meal. In yet another embodiment, a functionally active HIO polypeptide can rescue defective (including deficient) endogenous HIO polypeptide activity when expressed in a plant or in plant cells; the rescuing polypeptide may be from the same or from a different species as the species with the defective polypeptide activity. The disclosure also provides feed, meal, grain, food, or seed comprising the HIO polypeptide, or a fragment, derivative (variant), or ortholog or paralog thereof.

In another embodiment, a functionally active fragment of a full length HIO polypeptide (for example, a functionally active fragment of a native polypeptide having the amino acid sequence set forth as SEQ ID NO: 2, SEQ ID NO: 4, SEQ ID NO: 6, SEQ ID NO: 8, SEQ ID NO: 10, SEQ ID NO: 12, or SEQ ID NO: 14, or a naturally occurring ortholog or paralog thereof) retains one or more of the biological properties associated with the full-length HIO polypeptide, such as signaling activity, binding activity, catalytic activity, or cellular or extra-cellular localizing activity. A HIO fragment preferably comprises a HIO domain, such as a C- or N-terminal or catalytic domain, among others, and preferably comprises at least 10, preferably at least 20, more preferably at least 25, and most preferably at least 50 contiguous amino acids of a HIO protein. Functional domains of HIO genes are listed in column 6 of Table 2 and can be identified using the PFAM program (Bateman A et al., 1999, *Nucleic Acids Res.* 27:260-

262) or INTERPRO (Mulder et al., 2003, *Nucleic Acids Res.* 31, 315-318) program. Functionally active variants of full-length HIO polypeptides, or fragments thereof, include polypeptides with amino acid insertions, deletions, or substitutions that retain one of more of the biological properties associated with the full-length HIO polypeptide. In some cases, variants are generated that change the post-translational processing of an HIO polypeptide. For instance, variants may have altered protein transport or protein localization characteristics, or altered protein half-life, compared to the native polypeptide.

As used herein, the term "HIO nucleic acid" refers to any polynucleotide that when expressed in a plant causes an altered phenotype in any part of the plant, for example the seeds. In one embodiment, a HIO polynucleotide encompasses nucleic acids with the sequence provided in or complementary to the GenBank entry referenced in column 3 of Tables 2 and 3, which correspond to nucleic acid sequences set forth as SEQ ID NO: 1, SEQ ID NO: 3, SEQ ID NO: 5, SEQ ID NO: 7, SEQ ID NO: 9, SEQ ID NO: 11, or SEQ ID NO: 13, as well as functionally active fragments, derivatives, or orthologs or paralogs thereof. A HIO nucleic acid of this disclosure may be DNA, derived from genomic DNA or cDNA, or RNA.

In one embodiment, a functionally active HIO nucleic acid encodes or is complementary to a nucleic acid that encodes a functionally active HIO polypeptide. A functionally active HIO nucleic acid also includes genomic DNA that serves as a template for a primary RNA transcript (i.e., an mRNA precursor) that requires processing, such as splicing, before encoding the functionally active HIO polypeptide. A HIO nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO polypeptide, or an intermediate form. A HIO polynucleotide can also include heterologous coding sequences, for example, sequences that encode a marker included to facilitate the purification of the fused polypeptide, or a transformation marker. In another embodiment, a functionally active HIO nucleic acid is capable of being used in the generation of loss-of-function HIO phenotypes, for instance, via antisense suppression, co-suppression, etc. The disclosure also provides feed, meal, grain, food, or seed comprising a nucleic acid sequence that encodes an HIO polypeptide.

In one preferred embodiment, a HIO nucleic acid used in the disclosed methods comprises a nucleic acid sequence that encodes, or is complementary to a sequence that encodes, a HIO polypeptide having at least 50%, 60%, 70%, 75%, 80%, 85%, 90%, 95%, 97%, 98%, or 99% sequence identity to a disclosed HIO polypeptide sequence, for example the amino acid sequence set forth as SEQ ID NO: 2, SEQ ID NO: 4, SEQ ID NO: 6, SEQ ID NO: 8, SEQ ID NO: 10, SEQ ID NO: 12, or SEQ ID NO: 14.

In another embodiment, a HIO polypeptide comprises a polypeptide sequence with at least 50% or 60% identity to a disclosed HIO polypeptide sequence (for example, the amino acid sequence set forth as SEQ ID NO: 2, SEQ ID NO: 4, SEQ ID NO: 6, SEQ ID NO: 8, SEQ ID NO: 10, SEQ ID NO: 12, or SEQ ID NO: 14) and may have at least 70%, 80%, 85%, 90%, 95%, 97%, 98%, or 99% sequence identity to a disclosed HIO polypeptide sequence. In a further embodiment, a HIO polypeptide comprises 50%, 60%, 70%, 80%, 85%, 90%, 95%, 97%, 98%, or 99% sequence identity to a disclosed HIO polypeptide sequence, and may include a conserved protein domain of the HIO polypeptide (such as the protein domain(s) listed in column 6 of Table 2). In another embodiment, a HIO polypeptide comprises a polypeptide sequence with at least 50%, 60%, 70%, 80%, 85%, 90%, 95%, 97%, 98%, or 99% sequence identity to a functionally active fragment of the polypeptide referenced in column 4 of Table 2. In yet another embodiment, a HIO polypeptide comprises a polypeptide sequence with at least 50%, 60%, 70%, 80%, 90%, 95%, 97%, 98%, or 99% identity to the polypeptide sequence of the GenBank entry referenced in column 4 of Table 2 over its entire length and comprises a conserved protein domain(s) listed in column 6 of Table 2.

In another aspect, a HIO polynucleotide sequence is at least 50% to 60% identical over its entire length to a disclosed HIO nucleic acid sequence, such as the nucleic acid sequence set forth as SEQ ID NO: 1, SEQ ID NO: 3, SEQ ID NO: 5, SEQ ID NO: 7, SEQ ID NO: 9, SEQ ID NO: 11, or SEQ ID NO: 13, or nucleic acid sequences that are complementary to such a HIO sequence, and may comprise at least 70%, 80%, 85%, 90%, 95%, 97%, 98%, or 99% sequence identity to the disclosed HIO sequence, or a functionally active fragment thereof, or complementary sequences. In another embodiment, a disclosed HIO nucleic acid comprises a nucleic acid sequence as shown in SEQ ID NO: 1, SEQ ID NO: 3, SEQ ID NO: 5, SEQ ID NO: 7, SEQ ID NO: 9, SEQ ID NO: 11, or SEQ ID NO: 13, or nucleic acid sequences that are complementary to such a HIO sequence, and nucleic acid sequences that have substantial sequence homology to a such HIO sequences. As used herein, the phrase "substantial sequence homology" refers to those nucleic acid sequences that have slight or inconsequential sequence variations from such HIO sequences, i.e., the sequences function in substantially the same manner and encode an HIO polypeptide.

As used herein, "percent (%) sequence identity" with respect to a specified subject sequence, or a specified portion thereof, is defined as the percentage of nucleotides or amino acids in an identified sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., *J. Mol. Biol.,* 1990, 215:403-410) with search parameters set to default values. The HSP S and HSP S2 parameters are dynamic values and are established by the program itself depending upon the composition of the particular sequence and composition of the particular database against which the sequence of interest is being searched. A "percent (%) identity value" is determined by the number of matching identical nucleotides or amino acids divided by the sequence length for which the percent identity is being reported. "Percent (%) amino acid sequence similarity" is determined by performing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the disclosed HIO nucleic acid sequences (for example, the nucleic acid sequence set forth as SEQ ID NO: 1, SEQ ID NO: 3, SEQ ID NO: 5, SEQ ID NO: 7, SEQ ID NO: 9, SEQ ID NO: 11, or SEQ ID NO: 13). The stringency of hybridization can be controlled by temperature, ionic strength, pH, and the presence of denaturing agents such as formamide during hybridization and washing. Conditions routinely used are well known (see, e.g., *Current Protocol in Molecular Biology*, Vol. 1, Chap. 2.10, John Wiley & Sons, Publishers (1994); Sambrook et al., 1989, Molecular Cloning: A Laboratory Manual (Second Edition), Cold Spring Harbor Press, Plainview, N.Y.,).

In some embodiments, a nucleic acid molecule of the disclosure is capable of hybridizing to a nucleic acid molecule containing the disclosed nucleotide sequence under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18-20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO polypeptide can be produced. For example, codons may be selected to increase the rate at which expression of the polypeptide occurs in a particular host species, in accordance with the optimum codon usage dictated by the particular host organism (see, e.g., Nakamura et al., 1999, *Nucleic Acids Res.* 27:292). Such sequence variants may be used in the methods disclosed herein.

The disclosed methods may use orthologs (and/or paralogs) of a disclosed *Arabidopsis* HIO nucleic acid sequence. Representative putative orthologs (and/or paralogs) of each of the disclosed *Arabidopsis* HIO genes are identified in column 5 of Table 3, below. Methods of identifying the orthologs in other plant species are known in the art. In general, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, 1998, *Proc. Natl. Acad. Sci.*, 95:5849-5856; Huynen M A et al., 2000, *Genome Research*, 10:1204-1210).

Programs for multiple sequence alignment, such as CLUSTAL (Thompson J D et al., 1994, *Nucleic Acids Res.* 22:4673-4680) may be used to highlight conserved regions and/or residues of homologous (orthologous and/or paralogous) proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989, *Molecular Cloning: A Laboratory Manual* (Second Edition), Cold Spring Harbor Press, Plainview, N.Y.; Dieffenbach and Dveksler, 1995, *PCR Primer: A Laboratory Manual*, Cold Spring Harbor Laboratory Press, NY). For instance, methods for generating a cDNA library from the plant species of interest and probing the library with partially homologous gene probes are described in Sambrook et al. A highly conserved portion of the *Arabidopsis* HIO coding sequence may be used as a probe. HIO ortholog nucleic acids may hybridize to the nucleic acid of SEQ ID NO: 1, SEQ ID NO: 3, SEQ ID NO: 5, SEQ ID NO: 7, SEQ ID NO: 9, SEQ ID NO: 11, or SEQ ID NO: 13 under high, moderate, or low stringency conditions. After amplification or isolation of a segment of a putative ortholog, that segment may be cloned and sequenced by standard techniques and utilized as a probe to isolate a complete cDNA or genomic DNA clone.

Alternatively, it is possible to initiate an EST project to generate a database of sequence information for the plant species of interest. In another approach, antibodies that specifically bind known HIO polypeptides are used for ortholog (and/or paralog) isolation (see, e.g., Harlow and Lane, 1988, 1999, *Antibodies: A Laboratory Manual*, Cold Spring Harbor Laboratory Press, New York). Western blot analysis can determine that a HIO ortholog (i.e., a protein orthologous to a disclosed HIO polypeptide) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO nucleic acid and/or polypeptide sequences have been identified.

HIO nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991, *Methods Enzymol.* 204:125-39), may be used to introduce desired changes into a cloned nucleic acid.

In general, the methods disclosed herein involve incorporating the desired form of the HIO nucleic acid into a plant expression vector for transformation of plant cells, and the HIO polypeptide is expressed in the host plant. Transformed plants and plant cells expressing an HIO polypeptide express an altered phenotype and, in one specific, non-limiting example, may have high (increased) oil, high (increased) protein, and/or low (decreased) fiber content.

An "isolated" HIO nucleic acid molecule is other than in the form or setting in which it is found in nature, and is identified and separated from least one contaminant nucleic acid molecule with which it is ordinarily associated in the natural source of the HIO nucleic acid. However, an isolated HIO nucleic acid molecule includes HIO nucleic acid molecules contained in cells that ordinarily express the HIO polypeptide where, for example, the nucleic acid molecule is in a chromosomal location different from that of natural cells.

Generation of Genetically Modified Plants with an Altered Phenotype

The disclosed HIO nucleic acids and polypeptides may be used in the generation of transgenic plants having a modified or altered phenotype, for example an altered oil, protein, and/or fiber content phenotype. As used herein, an "altered oil content (phenotype)" may refer to altered oil content in any part of the plant. In a preferred embodiment, altered expression of the HIO gene in a plant is used to generate plants with a high oil content (phenotype). As used herein, an "altered total protein content (phenotype)" or an "altered digestible protein content (phenotype)" may refer to altered protein (total or digestible) content in any part of the plant. In a preferred embodiment, altered expression of the HIO gene in a plant is used to generate plants with a high (or increased) total or digestible protein content (phenotype). As used herein, an "altered fiber content (phenotype)" may refer to altered fiber content in any part of the plant. In a preferred embodiment, altered expression of the HIO gene in a plant is used to generate plants with a low (or decreased) fiber content (phenotype). The altered oil, protein and/or fiber content is often observed in seeds. Examples of a transgenic plant include plants comprising a plant transformation vector with a nucleotide sequence that encodes or is complementary to a sequence that encodes an HIO polypeptide having the amino acid sequence as set forth in SEQ ID NO: 2, SEQ ID NO: 4, SEQ ID NO: 6, SEQ ID NO: 8, SEQ ID NO: 10, SEQ ID NO: 12, or SEQ ID NO: 14, or an ortholog or paralog thereof.

Transgenic plants, such as corn, soybean and canola containing the disclosed nucleic acid sequences, can be used in the production of vegetable oil and meal. Vegetable oil is used in a variety of food products, while meal from seed is used as an animal feed. After harvesting seed from transgenic plants, the seed is cleaned to remove plant stalks and other material and then flaked in roller mills to break the hulls. The crushed seed is heated to 75-100° C. to denature hydrolytic enzymes, lyse the unbroken oil containing cells, and allow small oil droplets to coalesce. Most of the oil is then removed (and can be recovered) by pressing the seed material in a screw press. The remaining oil is removed from the presscake by extraction with and organic solvents, such as hexane. The solvent is removed from the meal by heating it to approximately 100° C. After drying, the meal is then granulated to a consistent form. The meal, containing the protein, digestible carbohydrate, and fiber of the seed, may be mixed with other materials prior to being used as an animal feed.

The methods described herein for generating transgenic plants are generally applicable to all plants. Although activation tagging and gene identification is carried out in *Arabidopsis*, the HIO nucleic acid sequence (or an ortholog, paralog, variant or fragment thereof) may be expressed in any type of plant. In a preferred embodiment, oil-producing plants produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*), and peanut (*Arachis hypogaea*), as well as wheat, rice and oat. Fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species may also be a source of unique fatty acids. In other embodiments, any plant expressing the HIO nucleic acid sequence can also express increased protein and/or decreased fiber content in a specific plant part or organ, such as in seeds.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to, as a strand of DNA, in a plasmid, or in an artificial chromosome. The introduction of the constructs into the target plant cells can be accomplished by a variety of techniques, including, but not limited to, *Agrobacterium*-mediated transformation, electroporation, microinjection, microprojectile bombardment, calcium-phosphate-DNA co-precipitation, or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.). A construct or vector may include a plant promoter to express the nucleic acid molecule of choice. In a preferred embodiment, the promoter is a plant promoter.

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as plants of the *Brassica* species, including canola and rapeseed, (De Block et al., 1989, *Plant Physiol.*, 91:694-701), maize (Ishida et al., 1996 *Nature Biotechnol.* 14:745-750, Zhang et al., 2002 *Plant Cell Rep.* 21:263-270) sunflower (Everett et al., 1987, *Bio/Technology*, 5:1201), soybean (Christou et al., 1989, *Proc. Natl. Acad. Sci. USA,* 86:7500-7504; Kline et al., 1987, *Nature,* 327:70), wheat, rice and oat.

Expression (including transcription and translation) of a HIO nucleic acid sequence may be regulated with respect to the level of expression, the tissue type(s) where expression takes place and/or developmental stage of expression. A number of heterologous regulatory sequences (e.g., promoters and enhancers) are available for controlling the expression of a HIO nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the nopaline synthase (NOS) promoter (Ebert et al., *Proc. Natl. Acad. Sci. (U.S.A.)* 84:5745-5749, 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324, 1987) and the CaMV 35S promoter (Odell et al., *Nature* 313:810-812, 1985 and Jones J D et al, 1992, *Transgenic Res.,* 1:285-297), the figwort mosaic virus 35S-promoter (U.S. Pat. No. 5,378,619), the light-inducible promoter from the small subunit of ribulose-1,5-bis-phosphate carboxylase (ss-RUBISCO), the Adh promoter (Walker et al., *Proc. Natl. Acad. Sci. (U.S.A.)* 84:6624-6628, 1987), the sucrose synthase promoter (Yang et al., *Proc. Natl. Acad. Sci. (U.S.A.)* 87:4144-4148, 1990), the R gene complex promoter (Chandler et al., *The Plant Cell* 1:1175-1183, 1989), the chlorophyll a/b binding protein gene promoter, the CsVMV promoter (Verdaguer B et al., 1998, *Plant Mol. Biol.,* 37:1055-1067), and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993, *Plant Mol. Bio.,* 21:625-640).

In one preferred embodiment, expression of the HIO nucleic acid sequence is under control of regulatory sequences from genes whose expression is associated with early seed and/or embryo development. Indeed, in a preferred embodiment, the promoter used is a seed-enhanced promoter. Examples of such promoters include the 5' regulatory regions from such genes as napin (Kridl et al., *Seed Sci. Res.* 1:209-219, 1991), globulin (Belanger and Kriz, *Genet.,* 129: 863-872, 1991, GenBank Accession No. L22295), gamma zein Z 27 (Lopes et al., *Mol Gen Genet.,* 247:603-613, 1995), L3 oleosin promoter (U.S. Pat. No. 6,433,252), phaseolin (Bustos et al., *Plant Cell,* 1(9):839-853, 1989), arcelin5 (U.S. Application No. 2003/0046727), a soybean 7S promoter, a 7Sα promoter (U.S. Application No. 2003/0093828), the soybean 7Sα' beta conglycinin promoter, a 7S α' promoter (Beachy et al., *EMBO J.,* 4:3047, 1985; Schuler et al., *Nucleic Acid Res.,* 10(24):8225-8244, 1982), soybean trypsin inhibitor (Riggs et al., *Plant Cell* 1(6):609-621, 1989), ACP (Baerson et al., *Plant Mol. Biol.,* 22(2):255-267, 1993), stearoyl-ACP desaturase (Slocombe et al., *Plant Physiol.* 104(4):167-176, 1994), soybean a' subunit of β-conglycinin (Chen et al., *Proc. Natl. Acad. Sci.* 83:8560-8564, 1986), *Vicia faba* USP (P-Vf.Usp, SEQ ID NO: 1, 2, and 3 in (U.S. Patent Application No. 2003/229918) and *Zea mays* L3 oleosin promoter (Hong et al., *Plant Mol. Biol.,* 34(3):549-555, 1997). Also included are the zeins, which are a group of storage proteins found in corn endosperm. Genomic clones for zein genes have been isolated (Pedersen et al., *Cell,* 29:1015-1026, 1982; and Russell et al., *Transgenic Res.* 6(2):157-168) and the promoters from these clones, including the 15 kD, 16 kD, 19 kD, 22 kD, 27 kD and genes, could also be used. Other promoters known to function, for example, in corn include the promoters for the following genes: waxy, Brittle, Shrunken 2, Branching enzymes I and II, starch synthases, debranching enzymes, oleosins, glutelins and sucrose synthases. Legume genes whose promoters are associated with early seed and embryo development include *V. faba* legumin (Baumlein et al., 1991, *Mol. Gen. Genet.* 225:121-8; Baumlein et al., 1992, *Plant J.* 2:233-9), *V. faba* usp (Fiedler et al., 1993, *Plant Mol. Biol.* 22:669-79), pea convicilin (Bown et al., 1988, *Biochem. J.* 251:717-26), pea lectin (dePater et al., 1993, *Plant Cell* 5:877-86), *P. vulgaris* beta phaseolin (Bustos et al., 1991, *EMBO J.* 10:1469-79), *P. vulgaris* DLEC2 and PHS [beta] (Bobb et al., 1997, *Nucleic Acids Res.* 25:641-7), and soybean beta-Conglycinin, 7S storage protein (Chamberland et al., 1992, *Plant Mol. Biol.* 19:937-49).

Cereal genes whose promoters are associated with early seed and embryo development include rice glutelin ("GluA-3," Yoshihara and Takaiwa, 1996, Plant Cell Physiol. 37:107-11; "GluB-1," Takaiwa et al., 1996, *Plant Mol. Biol.* 30:1207-21; Washida et al., 1999, *Plant Mol. Biol.* 40:1-12; "Gt3," Leisy et al., 1990, *Plant Mol. Biol.* 14:41-50), rice prolamin (Zhou & Fan, 1993, *Transgenic Res.* 2:141-6), wheat prolamin (Hammond-Kosack et al., 1993, *EMBO J.* 12:545-54), maize zein (Z4, Matzke et al., 1990, *Plant Mol. Biol.* 14:323-32), and barley *B-hordeins* (Entwistle et al., 1991, *Plant Mol. Biol.* 17:1217-31).

Other genes whose promoters are associated with early seed and embryo development include oil palm GLO7A (7S globulin, Morcillo et al., 2001, *Physiol. Plant* 112:233-243), *Brassica napus napin,* 2S storage protein, and napA gene (Josefsson et al., 1987, *J. Biol. Chem.* 262:12196-201; Stalberg et al., 1993, *Plant Mol. Biol.* 1993 23:671-83; Ellerstrom et al., 1996, *Plant Mol. Biol.* 32:1019-27), *Brassica napus* oleosin (Keddie et al., 1994, *Plant Mol. Biol.* 24:327-40), *Arabidopsis* oleosin (Plant et al., 1994, *Plant Mol. Biol.* 25:193-205), *Arabidopsis* FAE1 (Rossak et al., 2001, *Plant Mol. Biol.* 46:717-25), *Canavalia gladiata* conA (Yamamoto et al., 1995, *Plant Mol. Biol.* 27:729-41), and *Catharanthus roseus* strictosidine synthase (Str, Ouwerkerk and Memelink, 1999, *Mol. Gen. Genet.* 261:635-43). In another preferred embodiment, regulatory sequences from genes expressed during oil biosynthesis are used (see, e.g., U.S. Pat. No. 5,952,544). Alternative promoters are from plant storage protein genes (Bevan et al., 1993, *Philos. Trans. R. Soc. Lond. B. Biol. Sci.* 342:209-15). Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436.

In another embodiment, the endogenous HIO gene may be placed under the control of a transgenic transcription factor or used to design binding sites that modulates its expression. One such class of transcription factors are the $Cys_2$-$His_2$-zinc finger proteins (ZFPs). ZFPs are common DNA binding proteins and can be designed to specifically bind to specific DNA sequences (Beerli & Barbas, *Nat. Biotechnol.,* 2002, 20:135-141.; Gommans et al., *J. Mol. Biol.,* 2005, 354:507-519). Individual zinc-finger domains are composed of approximately 30 amino acids, are structurally conserved and can interact with 3-4 bp of DNA. A polypeptide containing multiple zinc-fingers designed to bind to a specific DNA sequence in the promoter of a HIO gene can be synthesized. The principles for designing the zinc finger domains to interact with specific DNA sequences have been described in Segal et al., (Segal et al., *Proc Natl Acad Sci USA.,* 1999, 96:2758-2763), Dreier et al. (Dreier et al., *J. Mol. Biol.,* 2000, 303:489-502), and Beerli and Barbas (Beerli & Barbas, *Nat.*

Biotechnol., 2002, 20:135-141). These DNA binding domains may be fused to effector domains to form a synthetic ZFP that may regulate transcription of genes to which they bind. Effector domains that can activate transcription include but are not limited to the acidic portion of the herpes simplex virus protein VP16 (Sadowski et al., *Nature.*, 1988, 335:563-564) and VP64 (Beerli et al., *Proc Natl Acad Sci USA.*, 1998, 95:14628-14633), and the NF-κB transcription factor p65 domain (Bae et al., *Nat. Biotechnol.*, 2003, 21:275-280., Liu et al., *J. Biol. Chem.*, 2001, 276:11323-11334). Effector domains that can repress transcription include but are not limited to mSIN3 and KRAB (Ayer et al., *Mol Cell Biol.*, 1996, 16:5772-5781, Beerli & Barbas, *Nat. Biotechnol.*, 2002, 20:135-141, Beerli et al., *Proc Natl Acad Sci USA*, 1998, 95:14628-14633, Margolin et al., *Proc Natl Acad Sci U.S.A.*, 1994, 91:4509-4513). These approaches have been shown to work in plants (Guan et al., *Proc Natl Acad Sci U.S.A.*, 2002, 99:13296-13301, Stege et al., *Plant J.*, 2002, 32:1077-1086, Van Eenennaam et al., *Metab Eng.*, 2004, 6:101-108).

In yet another aspect, in some cases it may be desirable to inhibit the expression of the endogenous HIO nucleic acid sequence in a host cell. Exemplary methods for practicing this aspect of the invention include, but are not limited to antisense suppression (Smith, et al., 1988, *Nature*, 334:724-726; van der Krol et al., 1988, *BioTechniques*, 6:958-976); co-suppression (Napoli, et al., 1990, *Plant Cell*, 2:279-289); ribozymes (PCT Publication WO 97/10328); and combinations of sense and antisense (Waterhouse, et al., 1998, *Proc. Natl. Acad. Sci. USA*, 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988, *Proc. Natl. Acad. Sci. USA*, 85:8805-8809), a partial cDNA sequence including fragments of 5' coding sequence, (Cannon et al., 1990, *Plant Mol. Biol.*, 15:39-47), or 3' non-coding sequences (Ch'ng et al., 1989, *Proc. Nat. Acad. Sci. USA*, 86:10006-10010). Cosuppression techniques may use the entire cDNA sequence (Napoli et al., 1990, *Plant Cell*, 2:279-289; van der Krol et al., 1990, *Plant Cell*, 2:291-299), or a partial cDNA sequence (Smith et al., 1990, *Mol. Gen. Genetics*, 224:477-481).

Standard molecular and genetic tests may be performed to further analyze the association between a nucleic acid sequence and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include over-expression, ectopic expression, expression in other plant species and gene knock-out (reverse genetics, targeted knock-out, viral induced gene silencing (VIGS; see, Baulcombe D, 1999, *Arch. Virol. Suppl.* 15:189-201).

In a preferred application expression profiling, generally by microarray analysis, is used to simultaneously measure differences or induced changes in the expression of many different genes. Techniques for microarray analysis are well known in the art (Schena M et al., *Science* 1995 270:467-470; Baldwin D et al., 1999, *Cur. Opin. Plant Biol.* 2(2):96-103; Dangond F, *Physiol Genomics* (2000) 2:53-58; van Hal N L et al., *J. Biotechnol.* (2000) 78:271-280; Richmond T and Somerville S, *Curr. Opin. Plant Biol.* 2000 3:108-116). Expression profiling of individual tagged lines may be performed. Such analysis can identify other genes that are coordinately regulated as a consequence of the over-expression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Phenotype

Additional methods are disclosed herein of generating a plant having an altered phenotype, wherein a plant is identified that has a mutation or an allele in its HIO nucleic acid sequence that results in an altered phenotype, compared to plants lacking the mutation or allele. The mutated plant can be generated using one or more mutagens, for example a chemical mutagen (such as ethylmethane sulfonate, methyl methane sulfonate, diethylsulfate, and nitrosoguanidine, or 5-bromo-deoxyuridine) radiation, or ultraviolet light. In some embodiments of the method, the mutated plant can be bred to generate progeny, which inherit the mutation or allele and have an altered phenotype. For example, provided herein is a method of identifying plants that have one or more mutations in the endogenous HIO nucleic acid sequence that confer an altered phenotype and generating progeny of these mutated plants having such a phenotype that are not transgenic. The mutated plants with an altered phenotype can have an altered oil, protein, and/or fiber content, or an altered seed meal content.

In one specific embodiment of the method, called "TILLING" (for targeting induced local lesions in genomes), mutations are induced in the seed of a plant of interest, for example, using EMS (ethylmethane sulfonate) treatment. The resulting plants are grown and self-fertilized, and the progeny are used to prepare DNA samples. PCR amplification and sequencing of the HIO nucleic acid sequence is used to identify whether a mutated plant has a mutation in the HIO nucleic acid sequence. Plants having HIO mutations may then be tested for altered oil, protein, and/or fiber content. To confirm that the HIO mutation causes the modified phenotype, experiments correlating the presence of the modified gene and the modified phenotype through genetic crosses can be performed. TILLING can identify mutations that alter the expression of specific genes or the activity of proteins encoded by these genes (see Colbert et al., 2001, *Plant Physiol.* 126:480-484; McCallum et al., 2000, *Nature Biotechnology* 18:455-457).

In another specific embodiment of the method, a candidate gene/Quantitative Trait Locus (QTLs) approach can be used in a marker-assisted breeding program to identify alleles of or mutations in the HIO nucleic acid sequence or orthologs (and/or paralogs) of the HIO nucleic acid sequence that may confer altered oil, protein, and/or fiber content (see Bert et al., *Theor Appl Genet.*, 2003 June; 107(1):181-9; and Lionneton et al., *Genome,* 2002 December; 45(6):1203-15). Thus, in a further aspect of the disclosure, a HIO nucleic acid is used to identify whether a plant having altered oil, protein, and/or fiber content has a mutation in an endogenous HIO nucleic acid sequence or has a particular allele that causes altered oil, protein, and/or fiber content in the plant.

While the disclosure has been described with reference to specific methods and embodiments, it will be appreciated that various modifications and changes may be made without departing from the disclosure. All publications cited herein are expressly incorporated herein by reference for the purpose of describing and disclosing compositions and methodologies that might be used in connection with the disclosure. All cited patents, patent applications, and sequence information in referenced public databases are also incorporated by reference.

EXAMPLES

Example 1

Generation of Plants with a HIO Phenotype by Transformation with an Activation Tagging Construct This Example describes the generation of transgenic plants with altered oil, protein, and/or fiber content.

Mutants were generated using the activation tagging "ACT-TAG" vector, pSKI015 (GI#6537289; Weigel D et al., 2000, *Plant Physiology,* 122:1003-1013). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed (from T1 plants) was harvested and sown in soil. T2 plants were exposed to the herbicide to kill plants lacking the ACTTAG vector. T2 plants were grown to maturity, allowed to self-fertilize and set seed. T3 seed (from the T2 plants) was harvested in bulk for each line.

T3 seed was analyzed by Near Infrared Spectroscopy (NIR) at the time of harvest. NIR spectra were captured using a Bruker 22 near infrared spectrometer. Bruker Software was used to estimate total seed oil, total seed protein and total seed fiber content using data from NIR analysis and reference methods according to the manufacturer's instructions. Oil content predicting calibrations were developed following the general method of AOCS Procedure Am1-92, Official Methods and Recommended Practices of the American Oil Chemists Society, 5th Ed., AOCS, Champaign, Ill. A NIR total protein content predicting calibration was developed using total nitrogen content data of seed samples following the general method of Dumas Procedure AOAC 968.06 (Official Methods of Analysis of AOAC International 17$^{th}$ Edition AOAC, Gaithersburg, Md.). A NIR fiber content predicting calibration was developed using crude fiber content data of seed samples following the general method of AOAC Official Method 962.09 (Official Methods of Analysis of AOAC International 17$^{th}$ Edition AOAC, Gaithersburg, Md.). A NIR oleic acid content predicting calibration was developed using oleic acid content data of seed samples determined by following the method of Browse et al. (1986 Anal. Biochem. 152:141-145). A NIR calibration curve for predicting digestible protein content was developed by measuring digestible protein content in a set of seed samples. Total protein content of in a known mass of seed was determined by measuring the total nitrogen content of the seed using the Dumas method (AOAC Official Method 968.06). The seed fiber is extracted from a separate seed sample using the method of Honig and Rackis, (1979, *J. Agri. Food Chem.,* 27: 1262-1266). The undigested protein remaining associated with the fiber is measured by the Dumas method (AOAC Official Method 968.06). Digestible protein content is determined by subtracting the amount of undigested protein associated with the fiber from the total amount of protein in the seed.

Oil, protein and fiber predictions from NIR spectra were compared for 82,274 individual ACTTAG lines. Subsequent to seed compositional analysis, the position of the ACTTAG element in the genome in each line was determined by inverse PCR and sequencing. 37,995 lines with recovered flanking sequences were considered in this analysis.

Seed oil, and protein values in 82,274 lines were determined by NIR spectroscopy and normalized to allow comparison of seed component values in plants grown at different times. Oil, protein and fiber values were normalized by calculating the average oil, protein and fiber values in seed from all plants planted on the same day (including a large number of other ACTTAG plants, including control, wild-type, or non-transgenic plants). The seed components for each line was expressed as a "percent relative value" which was calculated by dividing the component value for each line with the average component value for all lines planted on the same day (which should approximate the value in control, wild-type, or non-transgenic plants). The "percent relative protein" and "percent relative fiber" were calculated similarly.

Inverse PCR was used to recover genomic DNA flanking the T-DNA insertion. The PCR product was subjected to sequence analysis and placed on the genome using a basic BLASTN search and/or a search of the *Arabidopsis* Information Resource (TAIR) database (available at the publicly available website). Generally, promoters within 9 kb of the enhancers in the ACTTAG element are considered to be within "activation space." Genes with T-DNA inserts within coding sequences were not considered to be within "activation space." The ACTTAG lines identified are listed in column 3 of Table 1. In some cases more than one ACTTAG line is associated with a gene. The relative oil, protein, fiber and oleic acid values in columns 4, 5, 6 and 7, respectively, are determined by comparing the seed component in the plant identified in column 3 relative to other plants grown at the same time and not displaying the trait.

TABLE 1

| 1. Alias | 2. TAIR ID | 3. Plant ID | 4. Relative Oil (%) | 5. Relative Protein (%) | 6. Relative Fiber (%) | 7. Relative Oleic Acid |
|---|---|---|---|---|---|---|
| HIO2019 A | At1g17920 | IN081493 | 118.99 | 95.25 | 100.45 | 102.12 |
| HIO2019 A | At1g17920 | IN006312 | 109.05 | 95.89 | 108.83 | 109.05 |
| HIO2046 A | At5g59010 | IN089660 | 128.91 | 142.4 | 46.44 | |
| HIO2046 A | At5g59010 | IN047347 | 102.37 | 104.89 | 96.13 | 106.83 |

TABLE 1-continued

| 1. Alias | 2. TAIR ID | 3. Plant ID | 4. Relative Oil (%) | 5. Relative Protein (%) | 6. Relative Fiber (%) | 7. Relative Oleic Acid |
|---|---|---|---|---|---|---|
| HIO2079 A | At1g71410 | IN083604 | 131.01 | 83.85 | 99.94 | 139.75 |
| HIO2079 A | At1g71410 | IN007461 | 107.42 | 99.81 | 96.75 | 97.89 |
| HIO2080 C | At1g73660 | IN086720 | 127.93 | 86.29 | 117.27 | |
| HIO2080 C | At1g73660 | IN086720 | 127.93 | 86.29 | 117.27 | |
| HIO2080 C | At1g73660 | IN068250 | 109.31 | 92.95 | 104.37 | 109.68 |
| HIO2091 D | At1g09870 | IN086447 | 139.97 | 124.86 | 65.1 | |
| HIO2091 D | At1g09870 | IN037425 | 100.88 | 92.75 | 101.56 | 98.12 |
| HIO2097 A | At5g43250 | IN086712 | 123.39 | 107.47 | 98.3 | |
| HIO2097 A | At5g43250 | IN086698 | 119.63 | 94.3 | 103.68 | 203.11 |
| HIO2105 A | At3g07220 | IN005625 | 109.85 | 91.2 | 154.61 | 101.54 |

TABLE 2

| 1. Locus | 2. Tair ID | 3. Nucleic Acid seq. GI# | 4. Polypeptide seq. GI# | 5. Putative biochemical function/protein name | 6. Conserved protein domain |
|---|---|---|---|---|---|
| HIO2019 A | At1g17920 | gi\|42562137 SEQ ID NO: 1 | gi\|42562138 SEQ ID NO: 2 | homeobox-leucine zipper family protein/lipid-binding START domain-containing protein | IPR002913 Lipid-binding START<br><br>IPR001356 Homeobox<br>IPR000047 Helix-turn-helix motif, lambda-like repressor |
| HIO2046 A | At5g59010 | gi\|30697158 SEQ ID NO: 3 | gi\|22327962 SEQ ID NO: 4 | protein kinase-related | IPR000719 Protein kinase domain<br>IPR002290 Serine/threonine protein kinase |
| HIO2079 A | At1g71410 | gi\|30698795 SEQ ID NO: 5 | gi\|15217467 SEQ ID NO: 6 | protein kinase family protein | IPR000719 Protein kinase domain<br>IPR002290 Serine/threonine protein kinase<br>IPR000357 HEAT |
| HIO2091 D | At1g09870 | gi\|42561877 SEQ ID NO: 7 | gi\|18391081 SEQ ID NO: 8 | histidine acid phosphatase family protein | IPR000560 Histidine acid phosphatase |
| HIO2097 A | At5g43250 | gi\|18422310 SEQ ID NO: 9 | gi\|15239815 SEQ ID NO: 10 | transcription factor, putative | IPR003958 Transcription factor CBF/NF-Y/archaeal histone<br>IPR007124 Histone-fold/TFIID-TAF/NF-Y<br>IPR007125 Histone core |
| HIO2080 C | At1g73660 | gi\|30698956 SEQ ID NO: 11 | gi\|15219517 SEQ ID NO: 12 | protein kinase family protein | IPR000719 Protein kinase domain<br>IPR002290 Serine/threonine protein kinase |
| HIO2105 A | At3g07220 | gi\|42563574 SEQ ID NO: 13 | gi\|15231425 SEQ ID NO: 14 | transcriptional activator, putative [*Arabidopsis thaliana*] | IPR000253 Forkhead-associated domain |

TABLE 3

| 1. Locus | 2. Tair ID | 3. Nucleic Acid seq. GI# | 4. Polypeptide seq. GI# | 5. Orthologs | | |
|---|---|---|---|---|---|---|
| | | | | Nucleic Acid GI# | Polypeptide GI# | Species |
| HIO2019 A | At1g17920 | gi\|42562137 SEQ ID NO: 1 | gi\|42562138 SEQ ID NO: 2 | gi\|42563198 | gi\|15219456 | *Arabidopsis thaliana* |
| | | | | gi\|51872286 | gi\|51872287 | *Gossypium hirsutum* |
| | | | | gi\|51091189 | gi\|51091201 | *Oryza sativa* (japonica cultivar-group) |
| HIO2046 A | At5g59010 | gi\|30697158 SEQ ID NO: 3 | gi\|22327962 SEQ ID NO: 4 | gi\|30693983 | gi\|15232406 | *Arabidopsis thaliana* |
| | | | | gi\|30678717 | gi\|22328189 | *Arabidopsis thaliana* |
| | | | | gi\|42568239 | gi\|15237604 | *Arabidopsis thaliana* |
| HIO2079 A | At1g71410 | gi\|30698795 SEQ ID NO: 5 | gi\|15217467 SEQ ID NO: 6 | gi\|42562252 | gi\|42562253 | *Arabidopsis thaliana* |
| | | | | gi\|34912663 | gi\|34912664 | *Oryza sativa* (japonica cultivar-group) |
| | | | | gi\|13365563 | gi\|54290405 | *Oryza sativa* (japonica cultivar-group) |
| HIO2091 D | At1g09870 | gi\|42561877 SEQ ID NO: 7 | gi\|18391081 SEQ ID NO: 8 | gi\|50919436 | gi\|50919437 | *Oryza sativa* (japonica cultivar-group) |
| | | | | gi\|55730597 | gi\|55730598 | *Pongo pygmaeus* |
| | | | | GI:19923760 | GI:19923761 | *Homo sapiens* |
| HIO2097 A | At5g43250 | gi\|18422310 SEQ ID NO: 9 | gi\|15239815 SEQ ID NO: 10 | gi\|34906253 | gi\|34906254 | *Oryza sativa* (japonica cultivar-group) |
| | | | | gi\|55770762 | gi\|55770763 | *Oryza sativa* (japonica cultivar-group) |
| | | | | gi\|21313423 | gi\|21313424 | *Mus musculus* |
| HIO2080 C | At1g73660 | gi\|30698956 SEQ ID NO: 11 | gi\|15219517 SEQ ID NO: 12 | gi\|32527768 | gi\|32527769 | *Brassica juncea* |
| | | | | gi\|30685720 | gi\|22329643 | *Arabidopsis thaliana* |
| | | | | gi\|42415350 | gi\|51535180 | *Oryza sativa* (japonica cultivar-group) |
| HIO2105 A | At3g07220 | gi\|42563574 SEQ ID NO: 13 | gi\|15231425 SEQ ID NO: 14 | GI:50947858 | gi\|50947859 | *Oryza sativa* (japonica cultivar-group) |
| | | | | GI:51965035 | gi\|51965036 | *Oryza sativa* (japonica cultivar-group) |
| | | | | GI:18397890 | gi\|15231433 | *Arabidopsis thaliana* |

Example 2

Analysis of the *Arabidopsis* HIO Sequence

Sequence analyses were performed with BLAST (Altschul et al., 1990, *J. Mol. Biol.* 215:403-410), PFAM (Bateman et al., 1999, *Nucleic Acids Res.* 27:260-262), INTERPRO (Mulder et al. 2003 *Nucleic Acids Res.* 31, 315-318), PSORT (Nakai K, and Horton P, 1999, *Trends Biochem. Sci.* 24:34-6), and/or CLUSTAL (Thompson J D et al., 1994, *Nucleic Acids Res.* 22:4673-4680).

Example 3

Recapitulation Experiments

To test whether over-expression of the genes in Tables 1 and 2 alter the seed composition phenotype, protein, digestible protein, oil and fiber content in seeds from transgenic plants expressing these genes was compared with protein, digestible protein, oil and fiber content in seeds from non-transgenic control plants. To do this, the genes were cloned into plant transformation vectors behind the strong constitutive CsVMV promoter and the seed specific PRU promoter. These constructs were transformed into *Arabidopsis* plants using the floral dip method. The plant transformation vector contains a gene, which provides resistance to a toxic compound, and serves as a selectable marker. Seed from the transformed plants were plated on agar medium containing the toxic compound. After 7 days, transgenic plants were identified as healthy green plants and transplanted to soil. Non-transgenic control plants were germinated on agar medium, allowed to grow for 7 days and then transplanted to soil. Transgenic seedlings and non-transgenic control plants were transplanted to two inch pots that were placed in random positions in a 10 inch by 20 inch tray. The plants were grown to maturity, allowed to self-fertilize and set seed. Seed was harvested from each plant and its oil content estimated by Near Infrared (NIR) Spectroscopy using methods previously described. The effect of each construct on seed composition was examined in at least two experiments.

Table 4 lists constructs tested for causing a significant increase in oil, protein, digestible protein or a significant decrease in fiber were identified by a two-way Analysis of Variance (ANOVA) test at a p-value≦0.05. These constructs are listed in Table 4. The ANOVA p-values for Protein, Oil, Digestible Protein and Fiber are listed in columns 4-7, respectively. Those with a significant p-value are listed in bold. The Average values for Protein, Oil, Digestible Protein and Fiber are listed in columns 8-11, respectively and were calculated by averaging the average values determined for the transgenic plants in each experiment.

TABLE 4

| | | | ANOVA | | | | Average | | | |
| --- | --- | --- | --- | --- | --- | --- | --- | --- | --- | --- |
| 1. Alias | 2. Tair | 3. Contruct | 4. Protein | 5. Oil | 6. Digestible Protein | 7. Fiber | 8. Protein | 9. Oil | 10. Digestible Protein | 11. Fiber |
| HIO2019 A | At1g17920 | CsVMV::At1g17920 | 0.070 | 0.001 | 0.247 | 0.009 | 97.9% | 105.3% | 100.8% | 97.0% |
| HIO2019 A | At1g17920 | Pru::At1g17920 | 0.099 | 0.712 | 0.475 | 0.782 | 102.4% | 99.5% | 100.7% | 99.6% |
| HIO2046 A | At5g59010 | CsVMV::At5g59010 | 0.596 | 0.258 | 0.006 | 0.051 | 100.7% | 101.4% | 102.4% | 97.4% |
| HIO2046 A | At5g59010 | Pru::At5g59010 | 0.757 | 0.165 | 0.061 | 0.029 | 99.4% | 101.9% | 101.8% | 97.3% |
| HIO2079 A | At1g71410 | CsVMV::At1g71410 | 0.297 | 0.033 | 0.083 | 0.058 | 99.0% | 104.1% | 103.1% | 95.5% |
| HIO2079 A | At1g71410 | Pru::At1g71410 | 0.852 | 0.194 | 0.097 | 0.036 | 99.8% | 102.0% | 101.7% | 97.1% |
| HIO2080 C | At1g73660 | CsVMV::At1g73660 | 0.755 | 0.173 | 0.080 | 0.044 | 100.5% | 101.9% | 101.8% | 97.6% |
| HIO2080 C | At1g73660 | Pru::At1g73660 | 0.012 | 0.166 | 0.062 | 0.058 | 95.9% | 103.0% | 102.6% | 97.5% |
| HIO2091 D | At1g09870 | CsVMV::At1g09870 | 0.685 | 0.042 | 0.006 | 0.582 | 99.6% | 102.8% | 101.9% | 98.0% |
| HIO2091 D | At1g09870 | Pru::At1g09870 | 0.320 | 0.103 | 0.010 | 0.002 | 101.3% | 102.0% | 102.0% | 96.9% |
| HIO2097 A | At5g43250 | CsVMV::At5g43250 | 0.185 | 0.099 | 0.108 | 0.180 | 98.1% | 102.5% | 101.6% | 98.2% |
| HIO2097 A | At5g43250 | Pru::At5g43250 | 0.140 | 0.056 | 0.353 | 0.993 | 103.6% | 98.8% | 102.1% | 98.2% |
| HIO2105 A | At3g07220 | CsVMV::At3g07220 | 0.225 | 0.348 | 0.280 | 0.751 | 101.7% | 99.0% | 100.8% | 99.6% |
| HIO2105 A | At3g07220 | Pru::At3g07220 | 0.655 | 0.034 | 0.029 | 0.000 | 100.7% | 102.1% | 101.5% | 96.7% |

It is claimed:

1. A method of producing oil comprising:
growing a transgenic plant that comprises a heterologous polynucleotide that encodes a polypeptide comprising an amino acid sequence having at least 95% sequence identity to the sequence set forth in SEQ ID NO: 12 and conveying an increased oil phenotype on said transgenic plant when expressed in said plant, whereby the transgenic plant has said increased oil content phenotype, relative to a plant of the same species that does not comprise said heterologous polynucleotide; and
recovering oil from said transgenic plant.

2. The method of claim 1, wherein the oil is recovered from a seed of the transgenic plant and said seed comprises the heterologous polynucleotide.

3. A method of producing increased oil content in a plant, said method comprising:
introducing into progenitor cells of the plant a heterologous constitutive promoter operatively linked to a heterologous polynucleotide that encodes a polypeptide comprising an amino acid sequence having at least 95% sequence identity to the amino acid sequence set forth in SEQ ID NO: 12 and conveying an increased oil phenotype on said plant cells when expressed in said plant cells, to produce transformed cells overexpressing the polypeptide;
growing the transformed progenitor cells to produce a transgenic plant, wherein said heterologous polynucleotide is expressed in said transgenic plant;
identifying said transgenic plant that exhibits the increased oil content phenotype relative to a plant of the same species that does not comprise said heterologous polynucleotide; and
recovering oil from said transgenic plant.

4. The method of claim 3, wherein the heterologous polynucleotide encodes a polypeptide consisting of an amino acid sequence having at least 95% sequence identity to the amino acid sequence set forth in SEQ ID NO: 12.

5. The method of claim 3, wherein the heterologous polynucleotide encodes a polypeptide comprising the amino acid sequence set forth in SEQ ID NO: 12.

6. The method of claim 3, wherein the heterologous polynucleotide encodes a polypeptide consisting of the amino acid sequence set forth in SEQ ID NO: 12.

7. A method of producing oil comprising:
growing a transgenic plant that comprises a heterologous polynucleotide that encodes a polypeptide comprising an amino acid sequence having at least 95% sequence identity to the sequence set forth in SEQ ID NO: 12 and conveying a decreased fiber content phenotype and an increased oil phenotype on said plant when expressed in said plant;
identifying the transgenic plant that has said decreased fiber content phenotype and said increased oil phenotype, relative to a plant of the same species that does not comprise the heterologous polynucleotide; and
recovering oil from said transgenic plant.

8. The method of claim 7, wherein the heterologous polynucleotide encodes a polypeptide comprising the amino acid sequence set forth in SEQ ID NO: 12.

9. The method of claim 7, wherein the heterologous polynucleotide encodes a polypeptide consisting of the amino acid sequence set forth in SEQ ID NO: 12.

10. The method of claim 7, wherein the heterologous polynucleotide encodes a polypeptide consisting of an amino acid sequence having at least 95% sequence identity to the amino acid sequence set forth in SEQ ID NO: 12.

11. The method of claim 1, wherein the heterologous polynucleotide encodes a polypeptide consisting of an amino acid sequence having at least 95% sequence identity to the amino acid sequence set forth in SEQ ID NO: 12.

12. The method of claim 1, wherein the heterologous polynucleotide encodes a polypeptide comprising the amino acid sequence set forth in SEQ ID NO: 12.

13. The method of claim 1, wherein the heterologous polynucleotide encodes a polypeptide consisting of the amino acid sequence set forth in SEQ ID NO: 12.

* * * * *